(12) United States Patent
Pease et al.

(10) Patent No.: US 6,649,608 B2
(45) Date of Patent: Nov. 18, 2003

(54) 2,4-DI(HETERO-)ARYLAMINO (OXY)-5-SUBSTITUTED PYRIMIDINES AS ANTINEOPLASTIC AGENTS

(75) Inventors: Elizabeth Janet Pease, Macclesfield (GB); Gloria Anne Breault, Macclesfield (GB); Emma Jane Williams, Macclesfield (GB); Robert Hugh Bradbury, Macclesfield (GB); Jeffrey James Morris, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/203,154

(22) PCT Filed: Feb. 26, 2001

(86) PCT No.: PCT/GB01/00824

§ 371 (c)(1),
(2), (4) Date: Aug. 6, 2002

(87) PCT Pub. No.: WO01/64655

PCT Pub. Date: Sep. 7, 2001

(65) Prior Publication Data

US 2003/0149266 A1 Aug. 7, 2003

(30) Foreign Application Priority Data

Mar. 1, 2000 (GB) .............................................. 0004890

(51) Int. Cl.$^7$ .................... C07D 239/48; C07D 403/04; C07D 413/04; A61K 31/506; A61P 35/00

(52) U.S. Cl. .............................. 514/227.8; 514/231.5; 514/272; 514/275; 544/321; 544/324; 544/114; 544/60

(58) Field of Search .................. 544/321, 324, 544/114, 60; 514/272, 275, 231.5, 227.8

(56) References Cited

U.S. PATENT DOCUMENTS

| 4,983,608 A | 1/1991 | Effland et al. .............. 514/216 |
| 5,516,775 A | 5/1996 | Zimmermann et al. .. 514/224.2 |
| 5,521,184 A | 5/1996 | Zimmermann .............. 514/252 |
| 5,610,303 A | 3/1997 | Kimura et al. .............. 544/326 |
| 5,739,143 A | 4/1998 | Adams et al. .............. 514/275 |
| 5,859,041 A | 1/1999 | Liverton et al. ............ 514/396 |

FOREIGN PATENT DOCUMENTS

| CA | 2231765 | 9/1998 |
| EP | 0 363 002 | 4/1990 |
| EP | 0 379 806 B1 | 8/1990 |
| EP | 0 564 409 A | 10/1993 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 A | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |
| WO | 98/56788 | 12/1998 |
| WO | 99/01136 | 1/1999 |

(List continued on next page.)

OTHER PUBLICATIONS

Bennett, Cecil Textbook of Medicine, 20$^{th}$ edition, Vol 1, 1004–1010, 1997.*
Kornberg, Head Neck 20(8): 745–52, 1998.*
Boschelli et al., Synthesis and Tyrosine Kinase Inhibitory Activity of a Series of 2–Amino–8–H–pyrido[2,3–d]pyrimidines: Identifidation of Potent, Selective Platelet–Derived Growth Factor Receptor Tyrosine Kinase Inhibitors, J. Med. Chem., vol. 41, 1998, pp. 4365–4377.
Deady et al., "Reactions of some Quinazoline Compounds with Ethoxymethylenemalonic Acid Derivatives", J. Heterocyclic Chem., vol. 26, 1989, pp. 161–168.
Donnellan et al., "Cyclin E in human cancers", FASEB Journal, 13, 1999, pp. 773–780.
Ghosh, "2,4–Bis(arylamino)–6–methylpyrimidines as an antimicrobial agents", Chemical Abstracts No. 97712f, vol. 95, 1981, pp. 648.
Schmidt et al.; "A Convenient Synthesis of 2–substituted 4–Amino–5–pyrimidinecarbonitriles"; J. Heterocycle Chem., 1997, vol. 24, No. 5, pp. 1305–1307.
Zimmermann et al., Phenylamino–Pyrimidine (PAP) Derivatives: A New Class of Potent and Selective Inhibitors of Protein Kinase C (PKC), Arch. Pharm. Pharm. Med. Chem., vol. 329, 1996, pp. 371–376.

Primary Examiner—Richard L. Raymond
Assistant Examiner—Venkataraman Balasubramanian
(74) Attorney, Agent, or Firm—Morgan, Lewis & Bockius LLP

(57) ABSTRACT

Pyrimidine derivatives of the formula (I), wherein: $Q_1$ and $Q_2$ are independently selected from aryl or carbon linked heteroaryl optionally substituted as defined within; and one or both $Q_1$ and $Q_2$ are substituted on a ring carbon by one substituent of the formula (Ia) or (Ia'), wherein: Y, Z, n, m $Q_3$, G, $R^1$, are as defined within; and pharmaceutically acceptable salts and in in vivo hydrolysable esters thereof are described. Processes for their manufacture, pharmaceutical compositions and their use as cyclin-dependent serine/threonine kinase (CDK) and focal adhesion kinase (FAK) inhibitors are also described.

15 Claims, No Drawings

FOREIGN PATENT DOCUMENTS

| | | |
|---|---|---|
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/50250 | 10/1999 |
| WO | 00/12485 A | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 A | 7/2000 |
| WO | 00/44750 | 8/2000 |
| WO | 00/49018 | 8/2000 |
| WO | 00/53595 A | 9/2000 |
| WO | 00/55161 | 9/2000 |
| WO | 00/59892 | 10/2000 |
| WO | 00/78731 A1 | 12/2000 |
| WO | 01/14375 A1 | 3/2001 |
| WO | 01/29009 A1 | 4/2001 |
| WO | 01/30778 A1 | 5/2001 |
| WO | 01/37835 A1 | 5/2001 |
| WO | 01/47897 A1 | 7/2001 |
| WO | 01/47921 A1 | 7/2001 |
| WO | 01/60816 A1 | 8/2001 |
| WO | 01/64653 A1 | 9/2001 |
| WO | 01/64654 A1 | 9/2001 |
| WO | 01/64656 A1 | 9/2001 |
| WO | 01/72717 A1 | 10/2001 |
| WO | 02/04429 A1 | 1/2002 |
| WO | 02/20512 A1 | 3/2002 |

\* cited by examiner

2,4-DI(HETERO-)ARYLAMINO (OXY)-5-SUBSTITUTED PYRIMIDINES AS ANTINEOPLASTIC AGENTS

The invention relates to pyrimidine derivatives, or pharmaceutically acceptable salts or in vivo hydrolysable esters thereof, which possess cell-cycle inhibitory activity and are accordingly useful for their anti-cancer (such as anti-cell-proliferative, anti-cell migration and/or apoptotic) activity and are therefore useful in methods of treatment of a warm-blooded animal, such as man. The invention also relates to processes for the manufacture of said pyrimidine derivatives, to pharmaceutical compositions containing them and to their use in the manufacture of medicaments or use in the production of an anti-cancer (anti-cell-proliferation/migration and/or apoptotic) effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Although the precise details of how each of these factors combine to regulate CDK activity is poorly understood, the balance between the two dictates whether or not the cell will progress through the cell cycle.

The recent convergence of oncogene and tumour suppresser gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

Furthermore, it is believed that inhibition of focal adhesion kinase (FAK), which is involved in signal transduction pathways, induces apoptosis (cell-death) and/or inhibits cell migration and an inhibitor of FAK may therefore have value as an anti-cancer agent.

The present invention is based on the discovery that certain 2,4-pyrimidine compounds surprisingly inhibit the effects of cell cycle kinases showing selectivity for CDK2, CDK4 and CDK6, and also inhibit FAK and thus possess anti-cancer (anti-cell-migration/proliferation and/or apoptotic) properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to the invention there is provided a pyrimidine derivative of the formula (I):

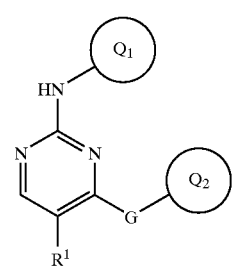

(I)

wherein:
$Q_1$ and $Q_2$ are independently selected from aryl or carbon linked heteroaryl; and one of $Q_1$ and $Q_2$ or both of $Q_1$ and $Q_2$ is substituted on a ring carbon by one substituent of the formula (Ia) or (Ia'):

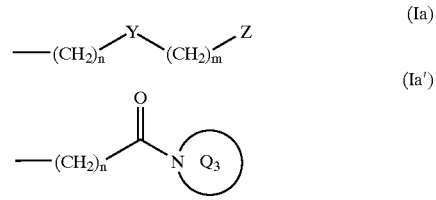

(Ia)

(Ia')

wherein:
Y is —NHC(O)— or —C(O)NH—;
Z is $R^aO$—, $R^bR^cN$—, $R^dS$—, $R^eR^fNNR^g$—, $C_{3-8}$cycloalkyl, phenyl or a heterocyclic group; wherein said phenyl, $C_{3-8}$cycloalkyl or heterocyclic group are optionally substituted on a ring carbon by one or more groups selected from $R^h$; and wherein if said heterocyclic group contains an —NH— moiety that nitrogen may be optionally substituted by a group selected from $R^i$;
$R^a, R^b, R^c, R^d, R^e, R^f$ and $R^g$ are independently selected from hydrogen, $C_{1-4}$alkyl, $C_{2-4}$alkenyl and $C_{3-8}$cycloalkyl; wherein said $C_{1-4}$alkyl, $C_{2-4}$alkenyl and $C_{3-8}$cycloalkyl are optionally substituted by one or more groups selected from $R^j$;
n is 0 or 1;
m is 1, 2 or 3;
$Q_3$ is a nitrogen linked heterocycle; wherein said heterocycle is optionally substituted on a ring carbon by one or more groups selected from $R^k$; and wherein if said heterocyclic group contains an —NH— moiety that nitrogen may be optionally substituted by a group selected from $R^m$;
G is —O— or —$NR_2$—;
$R^2$ is selected from hydrogen, $C_{1-6}$alkyl, $C_{3-6}$alkenyl and $C_{3-6}$alkynyl; wherein said $C_{1-6}$alkyl, $C_{3-6}$alkenyl and $C_{3-6}$alkynyl are optionally substituted by one or more groups selected from $R^n$;
$R^1$ is selected from hydrogen, halo, hydroxy, nitro, amino, N—($C_{1-3}$alkyl)amino, N,N-di-($C_{1-3}$alkyl)amino, cyano, trifluoromethyl, trichloromethyl, $C_{1-3}$alkyl [optionally substituted by 1 or 2 substituents independently selected from halo, cyano, amino, N—($C_{1-3}$alkyl)amino, N,N-di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, mercapto, $C_{1-3}$alkylsulphanyl, carboxy and $C_{1-3}$alkoxycarbonyl;
$Q_1$ is optionally substituted on a ring carbon by one to four substituents independently selected from halo, mercapto, nitro, formyl, formamido, carboxy, cyano, amino, ureido, carbamoyl, sulphamoyl, $C_{1-4}$alkyl, $C_{2-4}$alkenyl, $C_{2-4}$alkynyl [wherein said $C_{1-4}$alkyl, $C_{2-4}$alkenyl and $C_{2-4}$alkynyl are optionally substituted by one or more groups selected from $R^o$], $C_{1-4}$alkanoyl, $C_{1-4}$alkoxycarbonyl, heterocyclic group, $C_{1-4}$alkylS(O)$_a$ wherein a is 0 to 2 [optionally substituted by hydroxy], N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, N—$C_{1-4}$alkylamino, N,N-di-($C_{1-4}$alkyl)amino, N—($C_{1-4}$alkyl)sulphamoyl, N,N-di-($C_{1-4}$alkyl) sulphamoyl, N—$C_{1-4}$alkylcarbamoyl, N,N-di-($C_{1-4}$alkyl)carbamoyl and $C_{1-4}$alkanoylamino;

and also independently, or in addition to, the above substituents, $Q_1$ may be optionally substituted by one to two substituents independently selected from aryl, $C_{3-8}$cycloalkyl and a heterocyclic group; wherein said aryl, $C_{3-8}$cycloalkyl or heterocyclic group may be optionally substituted on a ring carbon by one or more groups selected from $R^p$; and wherein if said heterocyclic group contains an —NH— moiety that nitrogen may be optionally substituted by a group selected from $R^q$;

and also independently, or in addition to, the above substituents, $Q_1$ may be optionally substituted by one $C_{1-4}$alkoxy or by one hydroxy substituent;

$Q_2$ is optionally substituted on a ring carbon by one to four substituents independently selected from halo, hydroxy, mercapto, nitro, formyl, formamido, carboxy, cyano, amino, ureido, carbamoyl, sulphamoyl, $C_{1-4}$alkyl, $C_{2-4}$alkenyl, $C_{2-4}$alkynyl, $C_{1-4}$alkoxy [wherein said $C_{1-4}$alkyl, $C_{2-4}$alkenyl, $C_{2-4}$alkynyl and $C_{1-4}$alkoxy are optionally substituted by one or more groups selected from $R^r$], $C_{1-4}$alkanoyl, $C_{1-4}$alkoxycarbonyl, heterocyclic group, $C_{1-4}$alkylS(O)$_a$ wherein a is 0 to 2 [optionally substituted by hydroxy], N'—($C_{1-4}$alkyl)ureido, N',N'-di-($C_{1-4}$alkyl)ureido, N'—($C_{1-4}$alkyl)-N—($C_{1-4}$alkyl)ureido, N',N'-di-($C_{1-4}$alkyl)-N—($C_{1-4}$alkyl)ureido, N—$C_{1-4}$alkylamino, N,N-di-($C_{1-4}$alkyl)amino, N—($C_{1-4}$alkyl)sulphamoyl, N,N-di-($C_{1-4}$alkyl)sulphamoyl, N—$C_{1-4}$alkylcarbamoyl, N,N-di-($C_{1-4}$alkyl)carbamoyl, $C_{2-4}$alkenyloxy, $C_{2-4}$alkynyloxy, $C_{1-4}$alkanoylamino and a group of formula (Ia) or (Ia') as depicted above;

and also independently, or in addition to, the above substituents, $Q_2$ may be optionally substituted by one to two substituents independently selected from aryl, $C_{3-8}$cycloalkyl or a heterocyclic group; wherein said aryl, $C_{3-8}$cycloalkyl or heterocyclic group may be optionally substituted on a ring carbon by one or more groups selected from $R^s$; and wherein if said heterocyclic group contains an —NH— moiety that nitrogen may be optionally substituted by a group selected from $R^t$;

$R^j$, $R^n$, $R^o$ and $R^r$ are independently selected from hydroxy, halo, amino, cyano, formyl, formamido, carboxy, nitro, mercapto, carbamoyl, sulphamoyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy, $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N—($C_{1-4}$alkyl)sulphamoyl, N—($C_{1-4}$alkyl)$_2$sulphamoyl, N—($C_{1-4}$alkyl)carbamoyl, N—($C_{1-4}$alkyl)$_2$carbamoyl, phenyl, phenylthio, phenoxy, $C_{3-8}$cycloalkyl and a heterocyclic group; wherein said phenyl, phenylthio, phenoxy, $C_{3-8}$cycloalkyl or heterocyclic group may be optionally substituted on a ring carbon by one or more groups selected from $R^u$; and wherein if said heterocyclic group contains an —NH— moiety that nitrogen may be optionally substituted by a group selected from $R^v$;

$R^h$, $R^k$, $R^p$, $R^s$ and $R^u$ are independently selected from hydroxy, halo, amino, cyano, formyl, formamido, carboxy, nitro, mercapto, carbamoyl, sulphamoyl, $C_{1-4}$alkyl [optionally substituted by one or more groups selected from halo, cyano, amino, N—$C_{1-4}$alkylamino, N,N-di-($C_{1-4}$alkyl)amino or hydroxy], $C_{2-4}$alkenyl [optionally substituted by one or more groups selected from halo], $C_{2-4}$alkynyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy [optionally substituted by one or more groups selected from halo], $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N—($C_{1-4}$alkyl)sulphamoyl, N—($C_{1-4}$alkyl)$_2$sulphamoyl, phenyl, $C_{3-8}$cycloalkyl and a heterocyclic group; and $R^1$, $R^q$, $R^t$ and $R^v$ are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, benzyl, benzyloxycarbonyl, benzoyl and phenylsulphonyl;

or a pharmaceutically acceptable salt or in vivo hydrolysable ester thereof.

"Aryl" is a fully or partially unsaturated, mono or bicyclic carbon ring that contains 4–12 atoms. Preferably "aryl" is a monocyclic ring containing 5 or 6 atoms or a bicyclic ring containing 9 or 10 atoms. More preferably "aryl" is phenyl, naphthyl, tetralinyl or indanyl. Particularly "aryl" is phenyl, naphthyl or indanyl. More particularly "aryl" is phenyl.

A "carbon linked heteroaryl" is a fully unsaturated, 5- or 6-membered monocyclic ring or 9- or 10-membered bicyclic ring of which at least one atom is chosen from nitrogen, sulphur or oxygen. This ring is linked via a carbon atom to the —NH— (for $Q_1$) or G (for $Q_2$). Preferably "carbon linked heteroaryl" is furanyl, thienyl, pyrrolyl, oxazolyl, isoxazolyl, thiazolyl, isothiazolyl, imidazolyl, pyrazolyl, furazanyl, triazolyl, thiadiazolyl, pyridyl, pyrimidyl, pyrazinyl, pyridazinyl, triazinyl, indolyl, quinolyl or benzimidazolyl. More preferably "carbon linked heteroaryl" is pyridyl, thiazolyl or pyrazolyl. Particularly "carbon linked heteroaryl" is pyridyl.

A "heterocyclic group" is a saturated, partially saturated or unsaturated, mono or bicyclic ring containing 4–12 atoms of which at least one atom is chosen from nitrogen, sulphur or oxygen, which may, unless otherwise specified, be carbon or nitrogen linked, wherein a —CH$_2$— group can optionally be replaced by a —C(O)—, and a ring sulphur atom may be optionally oxidised to form S-oxide(s). Preferably a "heterocyclic group" is pyrrolidinyl, morpholino, piperidyl, pyridyl, pyranyl, pyrrolyl, isothiazolyl, indolyl, quinolyl, thienyl, furyl, 1,3-benzodioxolyl, thiadiazolyl, piperazinyl, thiazolidinyl, pyrrolidinyl, thiomorpholino, pyrazolyl, pyrrolinyl, homopiperazinyl, tetrahydropyranyl, imidazolyl, pyrimidyl, pyrazinyl, pyridazinyl, isoxazolyl, 4-pyridone, 1-isoquinolone, 2-pyrrolidone, 4-thiazolidone, imidazo[1,2-a]pyridine or 3-aza-8-oxabicyclo[3,2,1]hexane. More preferably a "heterocyclic group" is pyrrolidinyl, morpholino, piperidyl, indolyl, thienyl, furyl, piperazinyl, thiomorpholino, pyrazolyl, imidazolyl, 2-pyrrolidone, imidazo[1,2-a]pyridine or 3-aza-8-oxabicyclo[3,2,1]hexane.

A "nitrogen linked heterocycle" is a saturated, partially saturated or fully unsaturated, mono or bicyclic ring containing 4–12 atoms, one atom of which is a nitrogen atom (attached to form an amide as shown) and the other atoms are either all carbon atoms or they are carbon atoms and 1–3 heteroatoms chosen from nitrogen, sulphur or oxygen, wherein a —$CH_2$— group can optionally be replaced by a —C(O)— and a ring sulphur atom may be optionally oxidised to form the S-oxides. It will be appreciated that in forming this nitrogen link, the nitrogen atom is not quaternised, i.e. a neutral compound is formed. Preferably "nitrogen linked heterocycle" is pyrrol-1-yl, pyrrolin-1-yl, pyrrolidin-1-yl, imidazol-1-yl, imidazolin-1-yl, imidazolidin-1-yl, pyrazol-1-yl, pyrazolin-1-yl, pyrazolidin-1-yl, triazol-1-yl, piperidin-1-yl, piperazin-1-yl, morpholino, thiomorpholino, indol-1-yl, indolidin-1-yl or benzimidazol-1-yl. More preferably "nitrogen linked heterocycle" is piperidin-1-yl.

In this specification the term "alkyl" includes both straight and branched chain alkyl groups but references to individual alkyl groups such as "propyl" are specific for the straight chain version only. An analogous convention applies to other generic terms. "Halo" is fluoro, chloro, bromo and iodo.

Examples of $C_{2-4}$alkenyl are vinyl and allyl; examples of $C_{2-6}$alkenyl are $C_{3-5}$alkenyl, vinyl and allyl; an example of $C_{3-6}$alkenyl is allyl; an examples of $C_{3-6}$alkynyl are $C_{3-5}$alkynyl and propyn-2-yl; examples of $C_{2-4}$alkynyl are ethynyl and propyn-2-yl; examples of $C_{2-6}$alkynyl are ethynyl and propyn-2-yl; examples of $C_{1-4}$alkanoyl are acetyl and propionyl; examples of $C_{1-4}$alkoxycarbonyl are $C_{1-3}$alkoxycarbonyl, methoxycarbonyl, ethoxycarbonyl, propoxycarbonyl and tert-butoxycarbonyl; examples of $C_{1-4}$alkylene are methylene, ethylene and propylene; examples of $C_{1-4}$alkyl are $C_{1-3}$alkyl, methyl, ethyl, propyl, isopropyl, butyl, isobutyl, sec-butyl and tert-butyl; examples of $C_{1-6}$alkyl are methyl, ethyl, propyl, isopropyl, butyl, isobutyl, sec-butyl, tert-butyl and 3-methylbutyl; examples of $C_{1-4}$alkoxy are $C_{1-3}$alkoxy, methoxy, ethoxy, propoxy, isopropoxy and butoxy; an example of $C_{2-4}$alkenyloxy is allyloxy; an example of $C_{2-4}$alkynyloxy is propynyloxy; examples of $C_{1-4}$alkylS(O)$_a$ wherein a is 0 to 2 are $C_{1-3}$alkylsulphanyl, methylthio, ethylthio, propylthio, methylsulphinyl, ethylsulphinyl, propylsulphinyl, mesyl, ethylsulphonyl and propylsulphonyl; examples of N—$C_{1-4}$alkylcarbamoyl are N-methylcarbamoyl, N-ethylcarbamoyl and N-propylcarbamoyl; examples of N,N-di-($C_{1-4}$alkyl)-carbamoyl are N,N-dimethylcarbamoyl, N-ethyl-N-methylcarbamoyl and N,N-diethylcarbamoyl; examples of N—$C_{1-4}$alkylamino are N—($C_{1-3}$alkyl)amino, methylamino, ethylamino and propylamino; examples of N,N-di-($C_{1-4}$alkyl)amino are N,N-di-($C_{1-3}$alkyl)amino, dimethylamino, N-ethyl-N-methylamino, diethylamino, N-methyl-N-propylamino and dipropylamino; examples of $C_{1-4}$alkanoylamino are acetamido, propionamido and butyramido; examples of $C_{3-8}$cycloalkyl are cyclopropyl, cyclopentyl and cyclohexyl; examples of $C_{1-4}$alkanoyl are acetyl and propionyl; examples of $C_{1-4}$alkanoyloxy are acetyloxy and propionyloxy; examples of N'—($C_{1-4}$alkyl) ureido are N'-methylureido and N'-ethylureido; examples of N',N'-di-($C_{1-4}$alkyl)ureido are N',N'-dimethylureido, N',N'-diisopropylureido and N'-methyl-N'-propylureido; examples of N'—($C_{1-4}$alkyl)-N—($C_{1-4}$alkyl)ureido are N'-methyl-N-ethylureido and N'-methyl-N-methylureido; examples of N',N'-di-($C_{1-4}$alkyl)-N—($C_{1-4}$alkyl)ureido are N',N'-dimethyl-N-ethylureido and N'-methyl-N'-propyl-N-butylureido; examples of N—($C_{1-4}$alkyl)sulphamoyl are N-methylsulphamoyl and N-isopropylsulphamoyl; examples of N,N-di-($C_{1-4}$alkyl)sulphamoyl are N-methyl-N-ethylsulphamoyl and N,N-dipropylsulphamoyl; and examples of $C_{1-4}$alkylsulphonylamino are mesylamino, ethylsulphonylamino and propylsulphonylamino.

A suitable pharmaceutically acceptable salt of a pyrimidine derivative of the invention is, for example, an acid-addition salt of a pyrimidine derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a pyrimidine derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

Some compounds of the formula (I) may have chiral centres and/or geometric isomeric centres (E- and Z-isomers), and it is to be understood that the invention encompasses all such optical, diastereo-isomers and geometric isomers that possess CDK and/or FAK inhibitory activity.

The invention relates to any and all tautomeric forms of the compounds of the formula (I) that possess CDK and/or FAK inhibitory activity.

It is also to be understood that certain compounds of the formula (I) can exist in solvated as well as unsolvated forms such as, for example, hydrated forms. It is to be understood that the invention encompasses all such solvated forms which possess CDK and/or FAK inhibitory activity.

Particular preferred compounds of the invention comprise a pyrimidine derivative of the formula (I), or pharmaceutically acceptable salt or in vivo hydrolysable ester thereof, wherein $R^1$, $Q_1$, $Q_2$, and G have any of the meanings defined hereinbefore, or any of the following values. Such values may be used where appropriate with any of the definitions, claims or embodiments defined hereinbefore or hereinafter.

Preferably $Q_1$ and $Q_2$ are independently selected from phenyl, pyridyl, thiazolyl and pyrazolyl.

Preferably $Q_1$ is phenyl.

Preferably $Q_2$ is phenyl, pyridyl, thiazolyl or pyrazolyl.

More preferably $Q_2$ is phenyl or pyridyl.

Preferably $Q_1$ is phenyl and $Q_2$ is selected from phenyl, pyridyl, thiazolyl and pyrazolyl.

More preferably $Q_1$ is phenyl and $Q_2$ is selected from phenyl and pyridyl.

Preferably in the substituent (Ia) or (Ia'):

Y is —NHC(O)— or —C(O)NH—;

Z is $R^aO$—, $R^bR^cN$—, $R^dS$—, phenyl or a heterocyclic group; wherein said phenyl or heterocyclic group are optionally substituted on a ring carbon by one or more groups selected from $R^h$; and wherein if said heterocyclic group contains an —NH— moiety that nitrogen may be optionally substituted by a group selected from $R^i$;

$R^a$, $R^b$, $R^c$ and $R^d$ are $C_{1-4}$alkyl;

n is 0 or 1;

m is 1, 2 or 3; and $Q_3$ is a nitrogen linked heterocycle; wherein said heterocycle is optionally substituted on a ring carbon by one or more groups selected from $R^k$.

More preferably in the substituent (Ia) or (Ia'):

Y is —NHC(O)— or —C(O)NH—;

Z is $R^aO$—, $R^bR^cN$—, $R^dS$—, phenyl, pyrrolidinyl, morpholino, piperidyl, indolyl, thienyl, furyl [optionally substituted by one or more methyl], piperazinyl [optionally substituted on a ring nitrogen by methyl], thiomorpholino, pyrazolyl [optionally substituted by one or more methyl], imidazolyl [optionally substituted by one or more groups selected from groups selected from methyl and nitro], 2-pyrrolidone, imidazo[1,2-a]pyridine or 3-aza-8-oxabicyclo[3,2,1]hexane;

$R^a$, $R^b$, $R^c$ and $R^d$ are $C_{1-4}$alkyl;

n is 0 or 1;

m is 1, 2 or 3; and $Q_3$ is piperidin-1-yl optionally substituted by pyrrolidin-1-yl.

Particularly the substituent (Ia) or (Ia') is

N-[2-(3-aza-8-oxabicyclo[3,2,1]hex-3-yl)ethyl]carbamoyl, N-(2-di-n-butylaminoethyl)carbamoyl, N-(2-diethylaminoethyl)carbamoyl, N-(2-diisopropylaminoethyl)carbamoyl, N-[2-(3,5-dimethylpyrazol-1-yl)ethyl]carbamoyl, N-(2-indol-3-ylethyl)carbamoyl, N-(2-isopropylaminoethyl)carbamoyl, N-[2-(2-methyl-5-nitroimidazol-1-yl)ethyl]carbamoyl, N-(2-methylthioethyl)carbamoyl, N-(2-morpholinoethyl)carbamoyl, N-(2-piperidin-1-ylethyl)carbamoyl, N-(2-pyrrolidin-1-ylethyl)carbamoyl, N-(2-thien-2-ylethyl)carbamoyl, N-(2-thiomorpholinoethyl)carbamoyl, N-(3-n-butoxypropyl)carbamoyl, N-(3-di-n-butylaminopropyl)carbamoyl, N-(3-imidazol-1-ylpropyl)carbamoyl, N-[3-(4-methylpiperazin-1-yl)propyl]carbamoyl, N-(3-methylthiopropyl)carbamoyl, N-(3-morpholinopropyl)carbamoyl, N-[3-(2-oxpyrrolidin-1-yl)propyl]carbamoyl, N-(3-pyrrolidin-1-ylpropyl)carbamoyl, N-(2-di-isopropylaminoethyl)carbamoylmethyl, N-(2-morpholinoethyl)carbamoylmethyl, N-(4-dimethylaminobenzylamine)carbamoyl, N-(imidazo[1,2-a]pyrid-2-ylmethyl)carbamoyl, N-(5-methylfur-2-ylmethyl)carbamoyl, 4-(pyrrolidin-1-yl)piperidin-1-ylcarbonyl, 3-(dimethylamino)propanamide or 3-(isopropylamino)propanamide.

More particularly the substituent (Ia) or (Ia') is N-(2-isopropylaminoethyl)carbamoyl, N-2-pyrrolidin-1-ylethyl)carbamoyl or N-3-imidazol-1-ylpropyl)carbamoyl.

Preferably the substituent of formula (Ia) or (Ia') is in ring $Q_1$.

Preferably when $Q_1$ is phenyl the substituent of formula (Ia) or (Ia') is in either the para- or meta-position relative to the —NH—.

More preferably when $Q_1$ is phenyl the substituent of formula (Ia) or (Ia') is in the para-position relative to the —NH—.

In one aspect of the invention preferably G is —O—.

In a further aspect of the invention preferably G is —$NR^2$—.

In one aspect of the invention when G is —$NR^2$—, preferably $R^2$ is hydrogen.

In another aspect of the invention when G is —$NR^2$—, preferably $R^2$ is not hydrogen.

Preferably $R^1$ is fluoro, chloro, bromo, methyl or cyano.

More preferably $R^1$ bromo.

Preferably $Q_1$ is unsubstituted except by the substituent of formula (Ia) or (Ia').

Preferably $Q_2$ is unsubstituted or substituted by one or two groups selected from fluoro, bromo, methyl, methoxy, methylthio or hydroxymethyl.

More preferably $Q_2$ is unsubstituted or substituted by one or two groups selected from fluoro, methyl or hydroxymethyl.

Preferably $Q_2$ is phenyl, 2-hydroxymethylphenyl, 3-fluorophenyl, 3-methylphenyl, 4-fluorophenyl, 4-bromophenyl, 4-methoxyphenyl, 4-hydroxymethylphenyl, 4-methylthiophenyl, 3,4-difluorophenyl, pyrid-2-yl, 6-methylpyrid-2-yl, 4-methylthiazol-2-yl or 5-methylpyrazol-2-yl.

More preferably $Q_2$ is pyrid-2-yl, 6-methylpyrid-2-yl, 3-fluorophenyl or 2-hydroxymethylphenyl.

Therefore, in a preferred aspect of the invention there is provided a pyrimidine derivative of the formula (I) as depicted above, wherein:

$Q_1$ and $Q_2$ are independently selected from phenyl, pyridyl, thiazolyl and pyrazolyl; $Q_2$ is unsubstituted or substituted by one or two groups selected from fluoro, bromo, methyl, methoxy, methylthio or hydroxymethyl; and $Q_1$ is substituted on a ring carbon by a substituent of formula (Ia) or (Ia') as depicted above wherein:

Y is —NHC(O)— or —C(O)NH—;

Z is $R^aO$—, $R^bR^cN$—, $R^dS$—, phenyl or a heterocyclic group; wherein said phenyl or heterocyclic group are optionally substituted on a ring carbon by one or more groups selected from $R^h$; and wherein if said heterocyclic group contains an —NH— moiety that nitrogen may be optionally substituted by a group selected from $R^i$;

$R^a$, $R^b$, $R^c$ and $R^d$ are $C_{1-4}$alkyl;

n is 0 or 1;

m is 1, 2 or 3; and $Q_3$ is a nitrogen linked heterocycle; wherein said heterocycle is optionally substituted on a ring carbon by one or more groups selected from $R^k$.

G is —O— or —NH—; and $R^1$ is fluoro, chloro, bromo, methyl or cyano;

or pharmaceutically acceptable salt or in vivo hydrolysable ester thereof.

Therefore, in a more preferred aspect of the invention there is provided a pyrimidine derivative of the formula (I) as depicted above, wherein:

$Q_1$ is phenyl and $Q_2$ is pyrid-2-yl, 6-methylpyrid-2-yl, 3-fluorophenyl or 2-hydroxymethylphenyl; and $Q_1$ is substituted para to the —NH— linker by a group selected from N-(2-isopropylaminoethyl)carbamoyl, N-(2-pyrrolidin-1-ylethyl)carbamoyl or N-(3-imidazol-1-ylpropyl)carbamoyl;

G is —NH—; and $R^1$ is bromo;

or pharmaceutically acceptable salt or in vivo hydrolysable ester thereof.

In one aspect of the invention preferred compounds of the invention are those of Examples 41, 80, 82, 84, 85, 92, 94, 96, 114 or 115 or pharmaceutically acceptable salt or in vivo hydrolysable ester thereof.

In a further aspect of the invention preferred compounds of the invention include any one of the Examples or pharmaceutically acceptable salt or in vivo hydrolysable ester thereof.

Preferred aspects of the invention are those which relate to the compound or a pharmaceutically acceptable salt thereof.

A pyrimidine derivative of the formula (I), or a pharmaceutically acceptable salt or an in vivo hydrolysable ester thereof, may be prepared by any process known to be applicable to the preparation of chemically-related compounds. Such processes, when used to prepare a pyrimidine derivative of the formula (I), or a pharmaceutically acceptable salt or an in vivo hydrolysable ester thereof, are provided as a further feature of the invention and are illustrated by the following representative examples in which, unless otherwise stated $R^1$, $Q_1$, $Q_2$ and G have any of the meanings defined hereinbefore for a pyrimidine derivative of the formula (I) and unless another substituent is drawn on ring $Q_1$ or $Q_2$ the ring may bear any of the substituents described hereinbefore (optionally protected as necessary). Where a substituent is drawn on ring $Q_1$, this includes (unless stated otherwise) the possibilities of the substituent being on ring $Q_2$ in addition to, or instead of the substituent being on ring $Q_1$. Necessary starting materials may be obtained by standard procedures of organic chemistry (see for example, Advanced Organic Chemistry (Wiley-Interscience), Jerry March—also useful for general guidance on reaction conditions and reagents). The preparation of such starting materials is described within the accompanying non-limiting processes and Examples. Alternatively necessary starting materials are obtainable by analogous procedures to those illustrated which are within the ordinary skill of an organic chemist.

Thus, as a further feature of the invention there are provided the following processes which comprises of:

a) for compounds of formula (I) where G is —NR$^2$—; reacting a pyrimidine of formula (II):

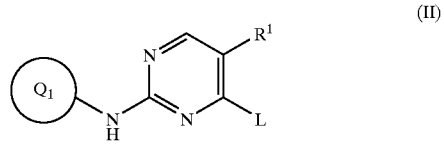

(II)

wherein L is a displaceable group as defined below, with a compound of formula (III):

(III)

where G is —NR$^2$—;

b) reaction of a pyrimidine of formula (IV):

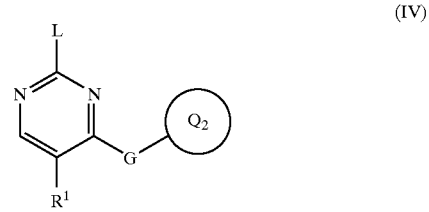

(IV)

wherein L is a displaceable group as defined below, with a compound of formula (V):

(V)

c) for compounds of formula (I) wherein the sidechain is of formula (Ia) and Y is —C(O)NH—; by reaction of an acid of formula (VI):

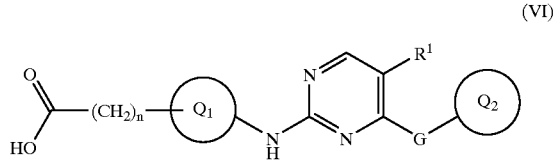

(VI)

or an activated derivative thereof; with an amine of formula (VII):

(VII)

d) for compounds of formula (I) wherein the sidechain is of formula (Ia) and Y is —NHC(O)— by reaction of an amine of formula (VIII):

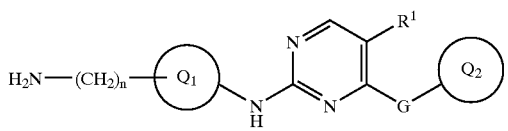 (VIII)

with an acid of formula (IX):

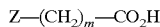 (IX)

or an activated derivative thereof;
e) for compounds of formula (I) wherein the sidechain is of formula (Ia'); by reaction of an acid of formula (VI) (or an activated derivative thereof) with an amine of formula (X):

 (X)

and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halo, sulphonyloxy or sulphur group, for example a chloro, bromo, methanesulphonyloxy, toluene-4-sulphonyloxy, mesyl, methylthio and methylsulphinyl.

Specific reaction conditions for the above reactions are as follows:

Process a)

Pyrimidines of formula (II) and compounds of formula (III) may be reacted together:

i) optionally in the presence of a suitable acid, for example an inorganic acid such as hydrochloric acid or sulphuric acid, or an organic acid such as acetic acid or formic acid. The reaction is preferably carried out in a suitable inert solvent or diluent, for example dichloromethane (DCM), acetonitrile, butanol, tetramethylene sulphone, tetrahydrofuran, 1,2-dimethoxyethane, N,N-dimethylformamide, N,N-dimethylacetamide or N-methylpyrrolidin-2-one, and at a temperature in the range, for example, 0° to 150° C., conveniently at or near reflux temperature; or ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to the following scheme:

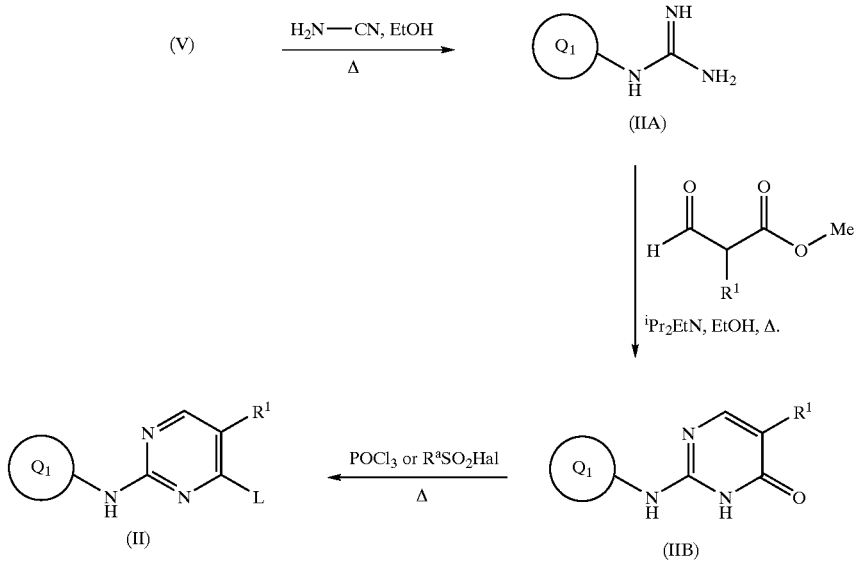

wherein $R^a$ is an optionally substituted alkyl or aryl group and L is a displaceable group as defined above. Preferably $R^a$ is methyl, ethyl or p-tolyl.

Compounds of formula (III) are commercially available or are prepared by processes known in the art.

Process b)

Pyrimidines of formula (IV) and anilines of formula (V) may be reacted together, i) in the presence of a suitable solvent for example a ketone such as acetone or an alcohol such as ethanol or butanol or an aromatic hydrocarbon such as toluene or N-methyl pyrrolidine, optionally in the presence of a suitable acid such as those defined above (or a suitable Lewis acid) and at a temperature in the range of 0° C. to reflux, preferably reflux; or ii) under standard Buchwald conditions as described above.

Pyrimidines of formula (IV) are prepared according to the following scheme:

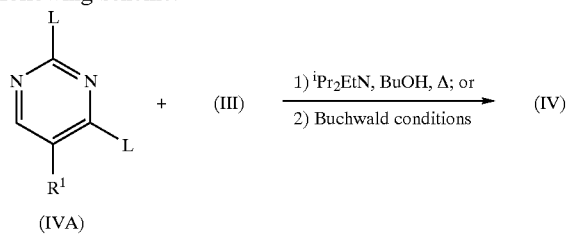

wherein L is a displaceable group as defined above.

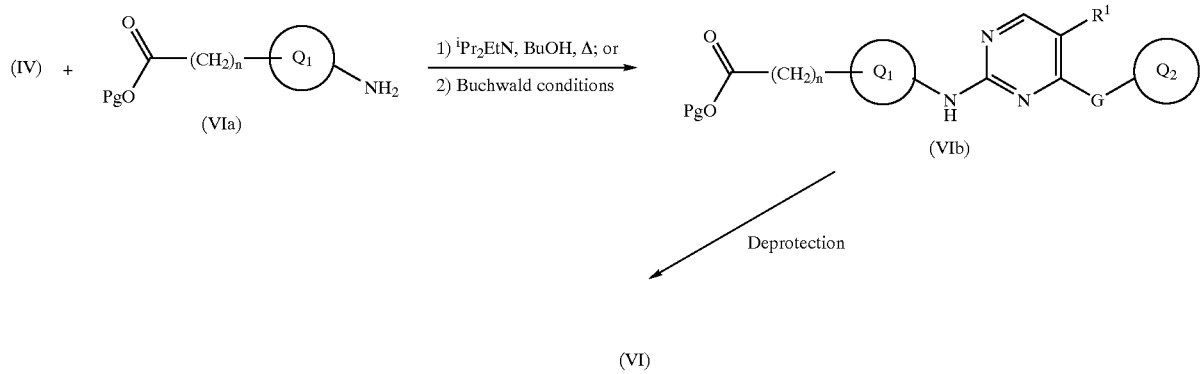

The anilines of formula (V) are commercially available or are prepared by processes known in the art.

Pyrimidines of the formula (IVA) are commercially available or may be prepared by, for example, reacting a compound of formula (IVA) in which L is —OH (i.e. a uracil), with $POCl_3$ to give a compound of formula (IVA) in which L is —Cl.

Process c)

Acids of formula (VI) and amines of formula (VII) may be coupled together in the presence of a suitable coupling reagent. Standard peptide coupling reagents known in the art can be employed as suitable coupling reagents, or for example carbonyldiimidazole and dicyclohexylcarbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Compounds of formula (VI) may be prepared according to the following scheme:

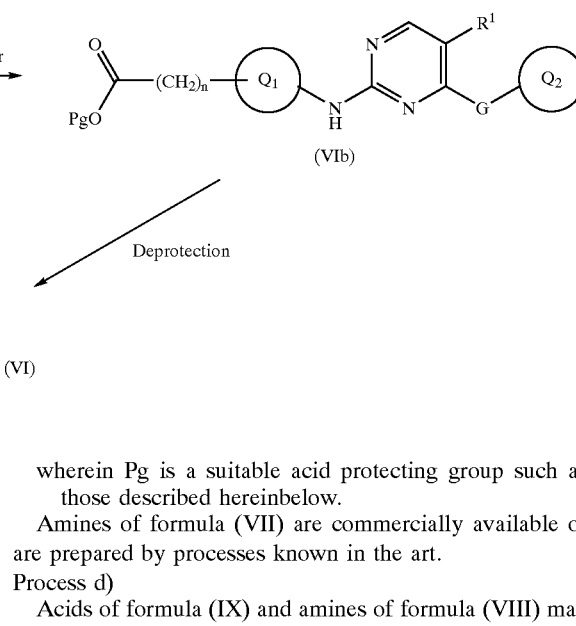

wherein Pg is a suitable acid protecting group such as those described hereinbelow.

Amines of formula (VII) are commercially available or are prepared by processes known in the art.

Process d)

Acids of formula (IX) and amines of formula (VIII) may be coupled together under the conditions described in process c) above.

Amines of formula (VIII) may be prepared according to the following scheme:

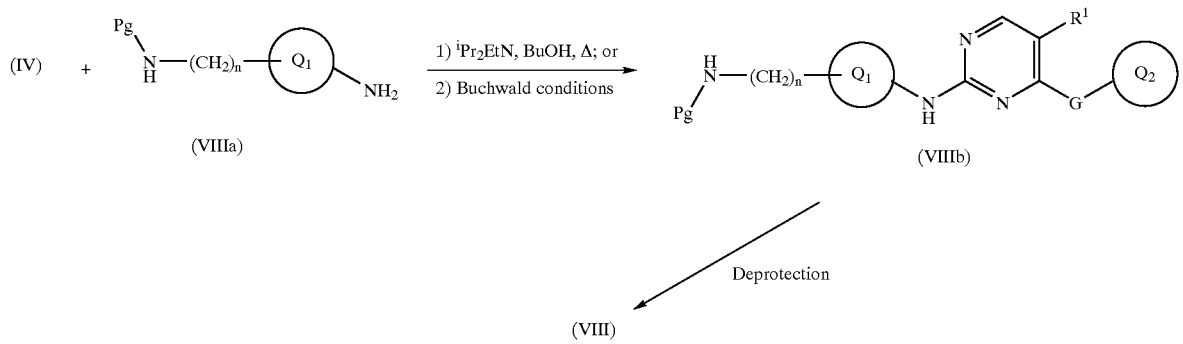

wherein Pg is a suitable amino protecting group such as those described hereinbelow.

Acids of formula (IX) are commercially available or are prepared by processes known in the art.

Process e)

Acids of formula (VI) and amines of formula (X) may be coupled together under the conditions described in process c) above.

Amines of formula (X) are commercially available or are prepared by processes known in the art.

Examples of conversions of a compound of formula (I) into another compound of formula (I) are:

i) where G is —$NR^2$—; conversion of $R^2$ as hydrogen into other $R^2$ for example:

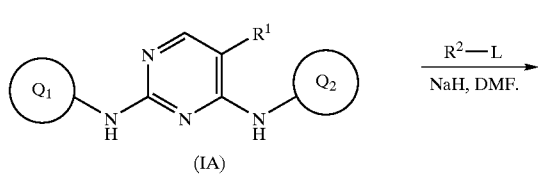

-continued

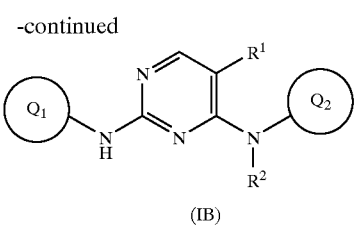

wherein L is a displaceable group;

ii) where G is $NR^2$; conversion of $R^2$ as a substituted side chain into another substituted side chain, for example:

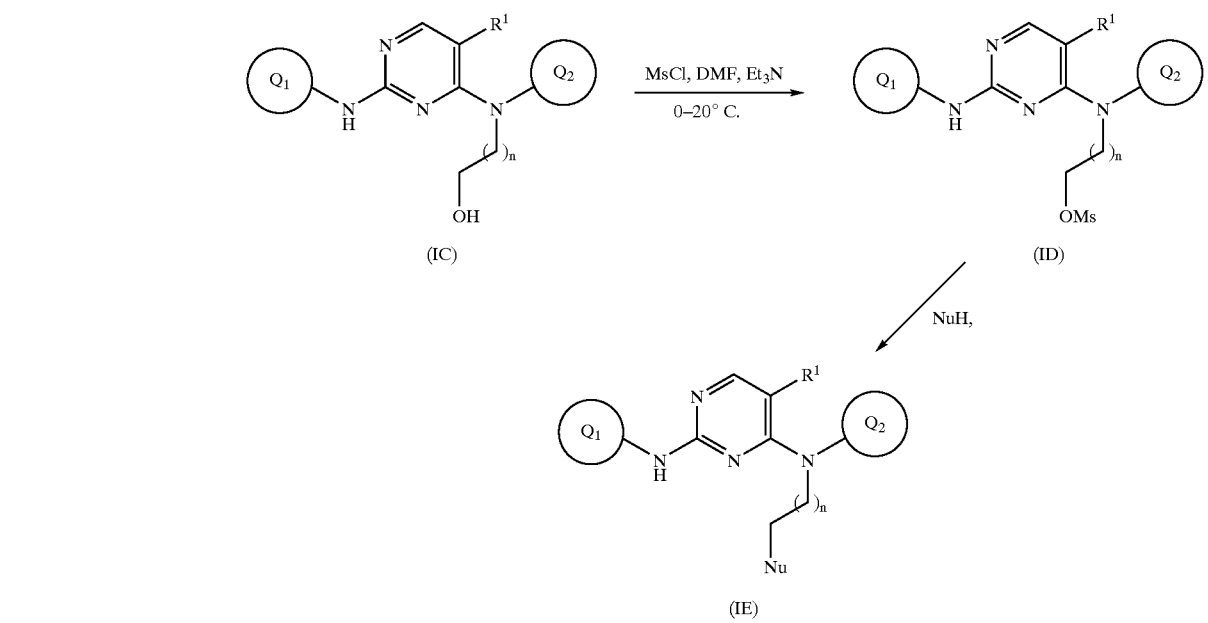

wherein Ms is methanesulphonyl, and Nu is a nucleophile that introduces a substituent that is an optional substituent for $R^2$ as defined in formula (I) (NB the hydroxyl moiety does not necessarily have to be on the terminal carbon as depicted above);

iii) conversion of one side chain of formula (Ia) into another side chain of formula (Ia).

iv) conversion of one value of $R^1$ into another value of $R^1$, using standard techniques, for example, conversion of $R^1$ as hydroxy into $C_{1-4}$alkoxy.

The skilled reader will appreciate that the formation of the side chain (Ia) or (Ia') described in Processes c), d) and e) above and of the sidechain $R^2$ in i) and ii) above may also be performed on intermediates. For example:

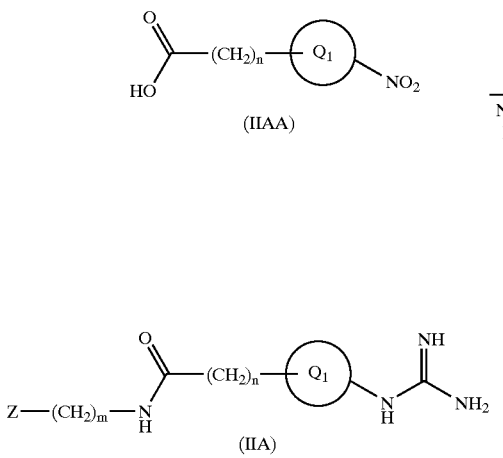

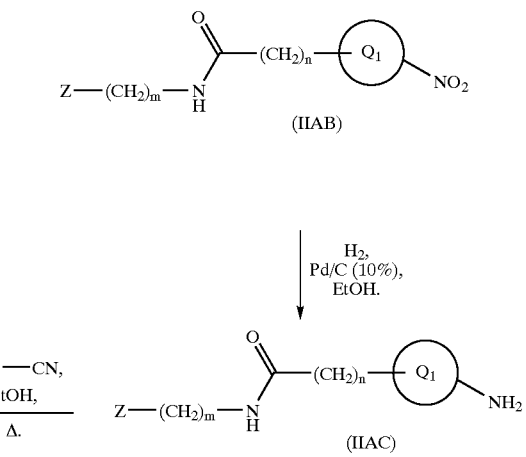

A preferred process of the invention is Process b).

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halo group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Many of the intermediates defined herein are novel, for example, those of the formula II and IV and these are provided as a further feature of the invention.

ASSAYS

As stated hereinbefore the pyrimidine derivative defined in the present invention possesses anti-cell-proliferation activity such as anti-cancer activity which is believed to arise from the CDK and/or FAK inhibitory activity of the compound. These properties may be assessed, for example, using the procedure set out below:

CDK4 Inhibition Assay

The following abbreviations have been used:
HEPES is N-(2-Hydroxyethyl)piperazine-N'-(2-ethanesulfonic acid)
DTT is Dithiothretiol
PMSF is Phenylmethylsulfonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma). In each well was placed the compound to be tested (diluted in DMSO and water to correct concentrations) and in control wells either p16 as an inhibitor control or DMSO as a positive control.

Approximately 0.5 μl of CDK4/Cyclin D1 partially-purified enzyme (amount dependent on enzyme activity) diluted in 25 μl incubation buffer was added to each well then 20 μl of GST-Rb/ATP/ATP33 mixture (containing 0.5 μg GST-Rb and 0.2 μM ATP and 0.14 μCi [γ-33-P]-Adenosine Triphosphate), and the resulting mixture shaken gently, then incubated at room temperature for 60 minutes.

To each well was then added 150 μL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124×g., for 5 minutes. The plates were read on a Topcount for 30 seconds per well.

The incubation buffer used to dilute the enzyme and substrate mixes contained 50 mM HEPES pH7.5, 10 mM MnCl$_2$, 1 mM DTT, 100 μM Sodium vanadate, 100 μM NaF, 10 mM Sodium Glycerophosphate, BSA (1 mg/ml final).

As a control, another known inhibitor of CDK4 may be used in place of p16.

Test Substrate

In this assay only part of the retinoblastoma (Science 1987 Mar 13;235(4794):1394–1399; Lee W. H., Bookstein R., Hong F., Young L. J., Shew J. Y., Lee E. Y.) was used, fused to a GST tag. PCR of retinoblastoma amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac I$^q$ gene for use in any *E. Coli* host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in *E. Coli* (BL21 (DE3) pLysS cells) using standard inducible expression techniques, and purified as follows.

*E. coli* paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl$_2$, 1 mM DTT, imM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK4 and Cyclin D1

CDK4 and Cyclin D1 were cloned from RNA from MCF-7 cell line (obtained from ATCC number:HTB22, breast adenocarcinoma line) as follows. The RNA was prepared from MCF-7 cells, then reverse transcribed using oligo dT primers. PCR was used to amplify the complete coding sequence of each gene [CDK4 amino acids 1–303; Ref. Cell Oct. 16, 1992; 71(2): 323–334; Matsushime H., Ewen M. E., Stron D. K, Kato J. Y., Hanks S. K., Roussel M. F., Sherr C. J. and Cyclin D1 amino acids 1–296; Ref Cold Spring Harb. Symp. Quant. Biol., 1991; 56:93–97; Arnold A., Motokura T., Bloom T., Kronenburg, Ruderman J., Juppner H., Kim H. G.].

After sequencing the PCR products were cloned using standard techniques into the insect expression vector pVL1393 (obtained from Invitrogen 1995 catalogue number: V1392-20). The PCR products were then dually expressed [using a standard virus Baculogold co-infection technique] into the insect *SF21* cell system (*Spodoptera Frugiperda* cells derived from ovarian tissue of the Fall Army Worm—Commercially available).

The following Example provides details of the production of Cyclin D1/CDK4 in SF21 cells (in TC100+10% FBS (TCS)+0.2% Pluronic) having dual infection MOI 3 for each virus of Cyclin D1 & CDK4.

Example Production of Cyclin D1/CDK4

SF21 cells grown in a roller bottle culture to 2.33×10$^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

10×500 ml were infected with JS303 Cyclin D1 virus titre—9×10E7 pfu/ml. JS304 CDK4 virus titre—1×10E8 pfu/ml.

$$Cyclin\ D1\ \frac{1.86 \times 10E6 \times 500 \times 3}{0.9 \times 10^8} =$$

31 ml of virus for each 500 ml. bottle.

$$CDK4\ \frac{1.86 \times 10E6 \times 500 \times 3}{1 \times 10^8} = 28\ ml\ of\ virus\ for\ each\ 500\ ml.\ bottle.$$

The viruses were mixed together before addition to the cultures, and the cultures returned to the roller rig 28° C.

After 3 days (72 hrs.) post infection the 5 Liters of culture was harvested. The total cell count at harvest was 1.58×10E6 cells/ml.(99% viable). The cells were spun out at 2500 rpm, 30 mins., 4° C. in Heraeus Omnifuge 2.0 RS in 250 ml lots. The supernatant was discarded. 20 pellets of ~4×10E8 cells/pellet were snap frozen in LN$_2$ and stored at –80° C. in CCRF cold room. The SF21 cells were then hypotonically lysed by resuspending in lysis buffer (50 mM HEPES pH 7.5, 10 mM magnesium chloride, 1 mM DTT, 10 mM glycerophosphate, 0.1 mM PMSF, 0.1 mM sodium fluoride, 0.1 mM sodium orthovanadate, 5 ug/ml aprotinin, 5 ug/ml leupeptin and 20% w/v sucrose), and adding ice cold deionised water. After centrifugation, the supernatant was loaded onto a Poros HQ/M 1.4/100 anion exchange column (PE Biosystems, Hertford, UK). CDK4 and Cyclin D1 were coeluted with 375 mM NaCl in lysis buffer, and their presence checked by western blot, using suitable anti-CDK4 and anti-Cyclin D1 antibodies (obtained from Santa Cruz Biotechnology, California, US).

p16 Control (Nature 366.:704–707: 1993: Serrano M. Hannon G J. Beach D)

p16 (the natural inhibitor of CDK4/Cyclin D1) was amplified from HeLa cDNA (Hela cells obtained from ATCC CCL2, human epitheloid carcinoma from cervix; Cancer Res. 12: 264, 1952), cloned into pTB 375 NBSE which had a 5' His tag, and transformed using standard techniques into BL21 (DE3) pLysS cells (obtained from Promega; Ref Studier F. W. and Moffat, B. A., J. Mol. Biol., 189, 113, 1986). A 1 liter culture was grown to the appropriate OD then induced with IPTG to express p16 overnight. The cells were then lysed by sonication in 50 mM sodium phosphate, 0.5M sodium chloride, PMSF, 0.5 $\mu$g/ml leupeptin and 0.5 $\mu$g/ml aprotinin. The mixture was spun down, the supernatant added to nickel chelate beads and mixed for 1½ hours. The beads were washed in sodium phosphate, NaCl pH 6.0 and p16 product eluted in sodium phosphate, NaCl pH 7.4 with 200 mM imidazole.

The pTB NBSE was constructed from pTB 375 NBPE as follows:

p TB375

The background vector used for generation of pTB 375 was pZEN0042 (see UK patent 2253852) and contained the tetA/tetR inducble tetracycline resistance sequence from plasmid RP4 and the cer stability sequence from plasmid pKS492 in a pAT153 derived background. pTB375 was generated by the addition of an expression cassette consisting of the T7 gene 10 promoter, multiple cloning site and T7 gene 10 termination sequence. In addition, a terminator sequence designed to reduce transcriptional readthrough from the background vector was included upstream of the expression cassette.

pTB 375 NBPE

The unique EcoRI restriction site present in pTB 375 was removed. A new multiple cloning site containing the recognition sequences for the restriction enzymes NdeI, BamHI, PstI and EcoRI was introduced into pTB 375 between the NdeI and BamHI sites destroying the original BamHI site present in pTB 375.

pTB 375 NBSE

A new multiple cloning site containing the recognition sequences for the restriction enzymes NdeI, BamHI, SmaI and EcoRI was introduced into pTB 375 NBPE between the NdeI and EcoRI sites. The oligonucleotide containing these restriction sites also contained 6 histidine codons located between the NdeI and BamHI sites in the same reading frame as the inititiator codon (ATG) present within the NdeI site.

By analogy to the above, assays designed to assess inhibition of CDK2 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

If using CDK2 with Cyclin E partial co-purification may be achieved as follows: Sf21 cells are resuspended in lysis buffer (50 mM Tris pH 8.2, 10 mM MgCl$_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant is loaded onto a Poros HQ/M 1.4/100 anion exchange column (PE Biosystems, Hertford, UK). CDK2 and Cyclin E are coeluted at the beginning of a 0–1 M NaCl gradient (run in lysis buffer minus protease inhibitors) over 20 column volumes. Co-elution is checked by western blot using both anti-CDK2 and anti-Cyclin E antibodies (Santa Cruz Biotechnology, California, US).

FAK3 Kinase Inhibition Assay

This assay determines the ability of a test compound to inhibit tyrosine kinase activity of human Focal Adhesion Kinase (FAK).

DNA encoding FAK is obtained by total gene synthesis (Edwards M, International Biotechnology Lab 5(3), 19–25, 1987) or by cloning. These are then expressed in a suitable expression system to obtain polypeptide with tyrosine kinase activity. For example, FAK, obtained by expression of recombinant protein in insect cells, was found to display intrinsic tyrosine kinase activity.

FAK (fall length human cDNA described by Andre et al (Biochemical and Biophysical Research Communications, 1993, 190 (1): 140–147; EMBL/GenBank Accession Number L05186)) was modified such that the resulting protein when translated had a 6-histidine tag at the N-terminus immediately preceding the start methionine. Active FAK protein has been previously expressed in a baculovirus system using a similar N-terminal 6-histidine tag (Protein Expression And Purification, 1996, 7: 12–18). The human FAK cDNA was cloned into the baculovirus transplacement vector, pFastbac 1 (Life Technologies), and the recombinant construct was co-transfected into insect cells (for example *Spodoptera frugiperda* 21(Sf21)) with viral DNA to prepare recombinant baculovirus (details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W.H. Freeman and Co, New York. Details specific to the use of the pFastbac ('Bac to Bac') system are provided in Anderson et al., 1995, FOCUS (Life Technologies Bulletin Magazine), 17, p53.)

For expression of biologically active human FAK protein, Sf12 cells were infected with plaque-pure FAK recombinant virus at a multiplicity of infection of 3 and harvested 48 hours later. Harvested cells were washed with ice cold phosphate buffered saline solution (PBS) (10 mM sodium phosphate pH7.4, 138 mM sodium chloride, 2.7 mM potassium chloride) then resuspended in ice cold lysis buffer (50 mM HEPES pH7.5, 1 mM Dithiothreitol, 100 uM Sodium Fluoride, 100 uM Sodium Orthovanadate, 10 mM Glycerophosphate, 100 uM Phenylmethylsulphonylfluoride (PMSF), 5 ug/ml Aprotinin, 5 ug/ml Leupeptin, 1% Tween; the PMSF being added just before use from a freshly-prepared 100 mM solution in methanol) using 250 µl lysis buffer per 10 million cells. The suspension was then incubated on ice for 15 minutes and centrifuged for 10 minutes at 13,000 rpm at 4° C. The supernatant (enzyme stock) was removed and aliquots made which were snap frozen in liquid nitrogen and then stored at −70° C. For a typical batch, stock enzyme was diluted 1 in 250 with enzyme diluent ((100 mM HEPES pH 7.4, 0.2 mM Dithiothreitol, 200 uM Sodium Orthovanadate, 0.1% Triton X-100) and 50 ml of freshly diluted enzyme was used for each assay well (see FAK3 protocol, below).

FAK3: In vitro Enzyme Assay Protocol

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Maxisorp 96 well immunoplates Life technologies, Cat. No. 439454A) which were sealed with plate sealers and left overnight at 4° C.

On the day of the assay the substrate solution was discarded and the assay plate wells were washed once with 200 µl PBST (PBS containing 0.05% v/v Tween 20) and once with 200 µl 50 mM Hepes pH7.4.

Test compounds were made up as 10 mM or 30 mM stocks in DMSO and then further diluted in glass distilled water diluted to a concentration 10 fold higher than the final assay concentration. 10 µl of diluted compound was transferred to wells in the washed assay plates. "No compound" control wells contained 10 µl glass distilled water instead of compound.

Forty microliters of 25 mM manganese chloride containing 6.25 µM adenosine-5'-triphosphate (ATP) was added to all test wells. To start the reactions 50 µl of freshly diluted enzyme was added to each well and the plates were incubated at 23C. for 90 minutes. Then the reaction was stopped by adding 100 µl of PBS containing 20 mM EDTA. The liquid was then discarded and the wells were washed twice with PBST.

One hundred microliters of mouse HRP-linked anti-phosphotyrosine antibody (Santa Cruz, Product SC 7020-HRP), diluted 1 in 1500 with PBST containing 0.5% w/v bovine serum albumin (BSA), was added to each well and the plates were incubated for 1 hour at room temperature before discarding the liquid and washing the wells twice with 200 µl PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the absorbance value of the "no compound" control wells, measured at 405 nm using a plate reading spectrophotometer, was approximately 1.0.

Dose response curves were generated from the absorbance readings using Origin Software. Compounds were ranked for potency using the Inhibitory Concentration 50 (IC50), as defined by Origin Software analysis.

Although the pharmacological properties of the compounds of the formula (I) vary with structural change, in general activity possessed by compounds of the formula (I) in the above assays may be demonstrated at $IC_{50}$ concentrations or doses in the range 250 µM to 1 nM.

When tested in the above in vitro assay the CDK4 inhibitory activity of Example 45 was measured as $IC_{50}$= 0.235 µM. When tested in the above in vitro assay the FAK inhibitory activity of Example 47 was measured as $IC_{50}$= 0.097 µM and that of Example 52 as $IC_{50}$=0.814 µM.

The in vivo activity of the compounds of the present invention may be assessed by standard techniques, for example by measuring inhibition of cell growth and assessing cytotoxicity. For example, further details may be found in the following references:

a) Attenution of the Expression of the Focal Adhesion Kinase induces Apoptosis in Tumor Cells. Xu L-h et al. Cell Growth & Differentiation (1996) 7, p413–418;

b) The COOH— Terminal Domain of the Focal Adhesion Kinase Induces Loss of Adhesion and Cell Death in Human Tumour Cells. Xu L-h et al. Cell Growth & Differentiation (1998) 9, p999–1005;

c) Inhibition of pp125-FAK in Cultured Fibroblasts Results in Apoptosis. Hungerford J. E et al. The Journal of Cell Biology (1996) 135, p1383–1390;

d) Inhibition of Focal Adhesion Kinase (FAK) Signalling in Focal Adhesions Decreases Cell Motility and Proliferation. Gilmore A. P and Romer L. H. Molecular Biology of the Cell (1996) 7, p1209–1224.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 µl in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% CO2) for three days.

At the end of three days TCA was added to the plates to a final concentration of 16% (v/v). Plates were then incubated at 4° C. for 1 hour, the supernatant removed and the plates washed in tap water. After drying, 100 µl SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formula (I), or a pharmaceutically acceptable salt or in vivo hydrolysable ester thereof, as defined hereinbefore in association with a pharmaceutically acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The pyrimidine will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a pyrimidine derivative of the formula (I), or a pharmaceutically acceptable salt or in vivo hydrolysable ester thereof, as defined hereinbefore for use in a method of prophylactic or therapeutic treatment of a warm-blooded animal, such as man.

We have found that the pyrimidine derivatives defined in the present invention, or a pharmaceutically acceptable salt or in vivo hydrolysable ester thereof, are effective cell cycle inhibitors (anti-cell proliferation agents), which property (without being bound by theory) is believed to arise from their CDK inhibitory properties. The compounds are also effective inhibitors of FAK. Accordingly the compounds of the present invention are expected to be useful in the treatment of diseases or medical conditions mediated alone or in part by CDK and/or FAK enzymes, i.e. the compounds may be used to produce a CDK and/or FAK inhibitory effect in a warm-blooded animal in need of such treatment. Thus the compounds of the present invention provide a method for treating the proliferation and/or migration of malignant cells characterised by inhibition of CDK and/or FAK enzymes, i.e. the compounds may be used to produce an anti-proliferative/migration effect mediated alone or in part by the inhibition of CDKs and/or FAK. The compounds may also be useful as FAK inhibitors by inducing cell-death (apoptosis). Such a pyrimidine derivative of the invention is expected to possess a wide range of anti-cancer properties as CDKs and/or FAK have been implicated in many common human cancers such as leukaemia and breast, lung, colon, rectal, stomach, prostate, bladder, pancreas and ovarian cancer. Thus it is expected that a pyrimidine derivative of the invention will possess anti-cancer activity against these cancers. It is in addition expected that a pyrimidine derivative of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDK and/or FAK, especially those tumours which are significantly dependent on CDK and/or FAK for their growth and spread, including for example, certain tumours of the colon, breast, prostate, lung, vulva and skin.

It is further expected that a pyrimidine derivative of the present invention will possess activity against other cell-proliferation/migration diseases in a wide range of other disease states including leukemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a pyrimidine derivative of the formula (I), or a pharmaceutically acceptable salt or in vivo hydrolysable ester thereof, as defined hereinbefore for use as a medicament; and the use of a pyrimidine derivative of the formula (I), or a pharmaceutically acceptable salt or in vivo hydrolysable ester thereof, as defined hereinbefore in the manufacture of a medicament for use in the production of an anti-cancer, cell cycle inhibitory (anti-cell-proliferation) effect and/or a FAK inhibitory (anti-cell migration and/or apoptosis inducing) effect in a warm-blooded animal such as man. Particularly, a cell cycle inhibitory effect is produced at the S or G1-S phase by inhibition of CDK2, CDK4 and/or CDK6, especially CDK4 and CDK6.

According to a further feature of this aspect of the invention there is provided a method for producing an anti-cancer, cell cycle inhibitory (anti-cell-proliferation) effect and/or a FAK inhibitory (anti-cell migration and/or apoptosis inducing) effect in a warm-blooded animal, such as man, in need of such treatment which comprises administering to said animal an effective amount of a pyrimidine derivative as defined immediately above. Particularly, an inhibitory effect is produced at the S or G1-S phase by inhibition of CDK2, CDK4 and/or CDK6, especially CDK4 and CDK6.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK and/or FAK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a pyrimidine derivative of the formula (I) as defined hereinbefore, or a pharmaceutically acceptable salt or in vivo hydrolysable ester thereof, and an additional anti-tumour substance as defined hereinbefore for the conjoint treatment of cancer. An anti-emetic may also be usefully administered, for example when using such conjoint treatment as described above.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other, pharmaceutical composition, process, method, use and medicament manufacture features, the alternative and preferred embodiments of the compounds of the invention described herein also apply.

The invention will now be illustrated in the following non limiting Examples, in which standard techniques known to the skilled chemist and techniques analogous to those described in these Examples may be used where appropriate, and in which, unless otherwise stated:

(i) evaporations were carried out by rotary evaporation in vacuo and work up procedures were carried out after removal of residual solids such as drying agents by filtration;

(ii) operations were carried out at ambient temperature, typically in the range 18–25° C. and in air unless stated, or unless the skilled person would otherwise operate under an atmosphere of an inert gas such as argon;

(iii) column chromatography (by the flash procedure) and medium pressure liquid chromatography (MPLC) were performed on Merck Kieselgel silica (Art. 9385) or on Merck Lichroprep RP-18 (Art. 9303) reversed-phase silica, obtained from E. Merck, Darmstadt, Germany; bond elute chromatography was performed using Varian Mega Bond Elut cartridges (10 g, order code 1225-6034), obtained from Varian Sample Preparation Products, California, USA;

(iv) yields are given for illustration only and are not necessarily the maximum attainable;

(v) the structures of the end products of the formula (I) were generally confirmed by nuclear (generally proton) magnetic resonance (NMR) and mass spectral techniques; proton magnetic resonance chemical shift values were measured in deuterated DMSOd$_6$ (unless otherwise stated) on the delta scale (ppm downfield from tetramethylsilane) using a Varian Gemini 2000 spectrometer operating at a field strength of 300 MHz, or a Bruker AM250 spectrometer operating at a field strength of 250 MHz; and peak multiplicities are shown as follows: s, singlet; d, doublet; dd, double doublet; t, triplet; tt, triple triplet; q, quartet; tq, triple quartet; m, multiplet; br, broad; mass spectrometry (MS) was performed by electrospray on a VG platform;

(vi) unless further details are specified in the text, analytical high performance liquid chromatography (HPLC) was performed on a Waters Spherisorb ODS1 25 cm column, at a flow rate of 2 ml/minute using acetonitrile/water/trifluoroacetic acid (60:40:0.1 v/v) as eluent, detection was at a wavelength of 254 nm, and data are quoted as retention time (RT) in minutes;

(vii) robotic synthesis was carried out using a Zymate XP robot, with solution additions via a Zymate Master Laboratory Station and stirred via a Stem RS5000 Reacto-Station at 25° C.;

(viii) work up and purification of reaction mixtures from robotic synthesis was carried out as follows: evaporations were carried out in vacuo using a Savant AES 2000; column chromatography was performed using either an Anachem Sympur MPLC or Jones Flashmaster MPLC systems on silica using Varian Mega Bond Elut cartridges; the structures of the final products were confirmed by LCMS on a Micromass OpenLynx system using the following and are quoted as retention time (RT) in minutes:

| Column | 4.6 mm × 10 cm Hichrom RPB 100Å |
|---|---|
| Solvent (System A) | I = 5% Methanol in Water + 0.1% formic acid, II = 5% Methanol in Acetonitrile + 0.1% formic acid |
| Solvent (System B) | I = Water + 0.1% formic acid, II = Acetonitrile + 0.1% formic acid |
| Run time | 10 minutes with a 6 minute gradient from 5–95% II |
| Wavelength | 254 nm, bandwidth 10 nm |
| Mass detector | Platform LC |

(ix) intermediates were not generally fully characterised and purity was assessed by thin layer chromatography (TLC), HPLC, infra-red (IR), MS or NMR analysis;

(x) where solutions are dried magnesium sulphate was the drying agent;

(xi) the following abbreviations may be used hereinbefore or hereinafter:

| DCM | dichloromethane; |
|---|---|
| DMF | N,N-dimethylformamide; |
| DMSO | dimethylsulphoxide; |

| | |
|---|---|
| NMP | N-methylpyrrolidin-2-one; |
| THF | tetrahydrofuran; and |

(xii) for the avoidance of doubt, where "precursor amines" are described and this amine contains more than one nitrogen, the resulting example formed is not a quaternary compound.

EXAMPLE 1

4-Anilino-5-chloro-2-{4-{N-[3-(imidazol-1-yl)propyl]carbamoyl}anilino}pyrimidine 4-Anilino-2-(4-carboxyanilino)-5-chloropyrimidine (Method 1; 170 mg, 0.5 mmol) was added to 1-(3-aminopropyl)imidazole (93.9 mg, 0.75 mmol) in a reaction tube. 1-Hydroxybenzotriazole (101 mg, 0.75 mmol) was added followed by N,N-diisopropylethylamine (130 mL 0.75 mmol) in DCM (4 ml). The mixture was flushed with argon and then stirred for 1 hour. 1-(3-Dimethylaminopropyl)-3-ethylcarbodiimide hydrochloride (105 mg, 0.55 mmol) in DCM (3 ml) was added and the mixture was stirred for 16 hours. The mixture was washed with saturated sodium bicarbonate solution (10 ml), water (10 ml) and saturated sodium chloride solution (10 ml), and the organic phase was loaded on a Varian Mega Bond Elut column. Elution with 0–10% 2.0M methanolic ammonia solution in DCM gave the product (11.6 mg, 5.2%). NMR: 2.0–2.15 (m, 2H), 3.0–3.1 (m, 2H), 4.25 (t, 2H), 7.25 (t, 1H), 7.4 (t, 2H), 7.6 (d, 4H), 7.7 (s, 1H), 7.75 (d, 2H), 7.85 (d, 1H), 8.3 (s, 1H), 8.6 (br t, 1H), 9.25 (d, 1H), 9.6 (br s, 1H), 10.3 (br s, 1H); LCMS (MH+): 448; HPLC (RT, System A): 6.16.

EXAMPLES 2–10

The following compounds were prepared using a Zymate XP robot by an analogous method to that described in Example 1, using 4-anilino-2-(4-carboxyanilino)-5-chloropyrimidine (Method 1) and the appropriate amine:

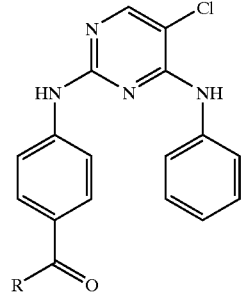

| Ex | R (Precursor amine) | LCMS (MH+) | HPLC[1] (RT) |
|---|---|---|---|
| 2 | 1-(3-Aminopropyl)-2-pyrrolidone | 465 | 6.5 |
| 3 | 4-(2-Aminoethyl)morpholine | 453 | 5.99 |
| 4 | 4-(3-Aminopropyl)morpholine | 467 | 6.04 |
| 5 | 1-(2-Aminoethyl)pyrrolidine | 437 | 6.12 |
| 6 | 2-(Diethylamino)ethylamine | 439 | 6.09 |
| 7 | 1-(3-Aminopropyl)-4-methylpiperazine | 480 | 5.7 |
| 8 | 1-(3-Aminopropyl)pyrrolidine | 451 | 5.95 |
| 9 | 3-(2-Aminoethyl)-3-aza-8-oxa-bicyclo[3,2,1]hexane[2] | 479 | 6.42 |
| 10 | 4-(2-Aminoethyl)thiomorpholine[3] | 469 | 6.27 |

[1]System A
[2]Precursor amine obtained as described in U.S. Pat. appl. 3856783
[3]Precursor amine obtained as described in J. Med. Chem. (1974), 17, 1232–4

EXAMPLES 11–20

The following compounds were prepared using a Zymate XP robot by an analogous method to that described in Example 1, using 4-anilino-5-bromo-2-(3-carboxyanilino)pyrimidine (Method 4) and the appropriate amine:

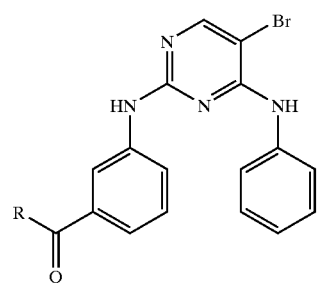

| Ex | R (Precursor amine) | LCMS (MH+) | HPLC[1] (RT) |
|---|---|---|---|
| 11 | 1-(3-Aminopropyl)pyrrolidine | 495 | 5.94 |
| 12 | 3-(2-Aminoethyl)-3-aza-8-oxa-bicyclo[3,2,1]hexane[2] | 523 | 6.25 |
| 13 | 4-(2-Aminoethyl)thiomorpholine[3] | 513 | 6.25 |
| 14 | 1-(3-Aminopropyl)imidazole | 492 | 5.8 |
| 15 | 1-(3-Aminopropyl)-2-pyrrolidinone | 509 | 6.4 |
| 16 | 4-(2-Aminoethyl)morpholine | 497 | 5.86 |
| 17 | 4-(3-Aminopropyl)morpholine | 511 | 6.36 |
| 18 | 1-(2-Aminoethyl)pyrrolidine | 481 | 5.99 |
| 19 | 2-(Diethylamino)ethylamine | 483 | 6.05 |
| 20 | 1-(3-Aminopropyl)-4-methylpiperazine | 524 | 5.68 |

[1]System A
[2]Precursor amine obtained as described in U.S. Pat. appl. 3856783
[3]Precursor amine obtained as described in J. Med. Chem. (1974), 17, 1232–4

EXAMPLES 21–30

The following compounds were prepared using a Zymate XP robot by an analogous method to that described in Example 1, using 5-bromo-2-(4-carboxyanilino)-4-(4-methoxyanilino)pyrimidine (Method 5) and the appropriate amine:

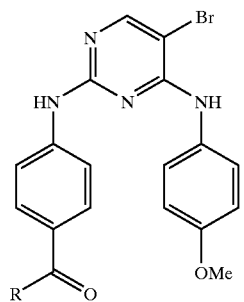

| Ex | R (Precursor amine) | LCMS (MH+) | HPLC[1] (RT) |
|---|---|---|---|
| 21 | 1-(3-Aminopropyl)imidazole | 522 | 6.09 |
| 22 | 1-(3-Aminopropyl)-2-pyrrolidinone | 539 | 6.53 |
| 23 | 4-(2-Aminoethyl)morpholine | 527 | 6.05 |
| 24 | 4-(3-Aminopropyl)morpholine | 541 | 60.1 |
| 25 | 1-(2-Aminoethyl)pyrrolidine | 511 | 6.05 |
| 26 | 2-(Diethylamino)ethylamine | 513 | 6.16 |
| 27 | 1-(3-Aminopropyl)-4-methylpiperazine | 554 | 5.75 |
| 28 | 1-(3-Aminopropyl)pyrrolidine | 525 | 6.01 |
| 29 | 3-(2-Aminoethyl)-3-aza-8-oxabicyclo[3,2,1]-hexane[2] | 553 | 6.43 |
| 30 | 4-(2-Aminoethyl)thiomorpholine[3] | 543 | 6.32 |

[1]System A
[2]Precursor amine obtained as described in U.S. Pat. appl. 3856783
[3]Precursor amine obtained as described in J. Med. Chem. (1974), 17, 1232–4

EXAMPLES 31–40

The following compounds were prepared using a Zymate XP robot by an analogous method to that described in Example 1, using 5-bromo-2-(4-carboxyanilino)-4-(4-methoxyphenoxy)pyrimidine (Method 26) and the appropriate amine:

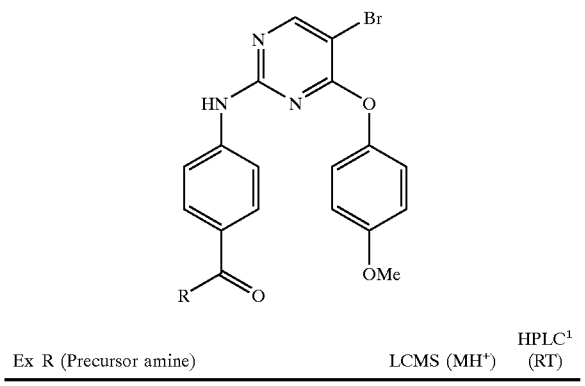

| Ex | R (Precursor amine) | LCMS (MH+) | HPLC[1] (RT) |
|---|---|---|---|
| 31 | 1-(3-Aminopropyl)imidazole | 523 | 6.82 |
| 32 | 1-(3-Aminopropyl)-2-pyrrolidinone | 540 | 7.19 |
| 33 | 4-(2-Aminoethyl)morpholine | 528 | 6.75 |
| 34 | 4-(3-Aminopropyl)morpholine | 542 | 6.45 |
| 35 | 1-(2-Aminoethyl)pyrrolidine | 512 | 6.79 |
| 36 | 2-(Diethylamino)ethylamine | 514 | 6.86 |
| 37 | 1-(3-Aminopropyl)-4-methylpiperazine | 555 | 6.55 |
| 38 | 1-(3-Aminopropyl)pyrrolidine | 526 | 6.97 |
| 39 | 3-(2-Aminoethyl)-3-aza-8-oxa-bicyclo[3,2,1]hexane[2] | 554 | 6.91 |
| 40 | 4-(2-Aminoethyl)thiomorpholine[3] | 544 | 6.95 |

[1]System A
[2]Precursor amine obtained as described in U.S. Pat. appl. 3856783
[3]Precursor amine obtained as described in J. Med. Chem. (1974), 17, 1232–4

EXAMPLES 41–58

The following compounds were prepared using a Zymate XP robot by an analogous method to that described in Example 1, using 4-anilino-5-bromo-2-(4-carboxyanilino) pyrimidine (Method 6) and the appropriate amine:

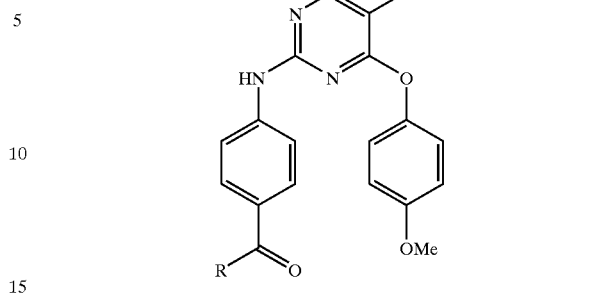

| Ex | R (Precursor amine) | LCMS (MH+) | HPLC[1] (RT) |
|---|---|---|---|
| 41 | 1-(3-Aminopropyl)imidazole | 492 | 5.9 |
| 42 | N-(3-Aminopropyl)-2-pyrrolidinone | 509 | 6.3 |
| 43 | Tryptamine | 527 | 6.7 |
| 44 | 4-(3-Aminopropyl)morpholine | 511 | 5.9 |
| 45 | 1-(2-Aminoethyl)piperidine | 495 | 6.1 |
| 46 | 1-(2-Aminoethyl)pyrrolidine | 481 | 6.0 |
| 47 | 3-(Di-n-butylamino)propylamine | 553 | 6.4 |
| 48 | 3-(n-Butoxy)propylamine | 498 | 7.0 |
| 49 | 3-(Methylthio)propylamine | 472 | 6.6 |
| 50 | 2-(Di-n-butylamino)ethylamine | 539 | 6.5 |
| 51 | 2-(Thien-2-yl)ethylamine | 494 | 6.8 |
| 52 | 4-(Pyrrolidin-1-yl)piperidine | 521 | 5.9 |

-continued

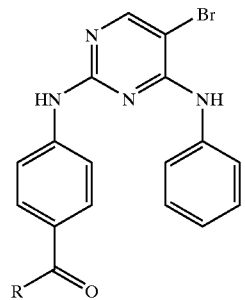

| Ex | R (Precursor amine) | LCMS (MH+) | HPLC[1] (RT) |
|---|---|---|---|
| 53 | 2-Aminomethylimidazo[1,2-a]pyridine | 514 | 6.1 |
| 54 | 4-(2-Aminoethyl)morpholine | 497 | 5.9 |
| 55 | 1-Aminoethyl-3,5-dimethylpyrazole | 506 | 6.5 |
| 56 | 2-(Methylthio)ethylamine | 458 | 76 |
| 57 | 1-(2-Aminoethyl)-2-methyl-5-nitroimidazole | 537 | 6.4 |
| 58 | 2-Methylamine-5-methylfuran | 478 | 6.7 |

[1]System B
[2]Precursor amine obtained as described in Heterocycl. Commun. (1996), 2, 241–246
[3]Precursor amine obtained as described in Recl. Trav. Chim. Pays-Bas (1992), 111, 371–8
[4]Precursor amine obtained as described in Eur. J. Med. Chem. - Chim. Ther. (1975), 10, 171–7

EXAMPLE 59

5-Bromo-4-(4-fluoroanilino)-2-(4-{N-[3-(2-oxopyrrolidin-1-yl)propyl]carbamoyl}anilino)pyrimidine 1-(3-Dimethylaminopropyl)-3-ethylcarbodiimide hydrochloride (52 mg, 0.27 mmol) was added to a mixture of 5-bromo-2-(4-carboxyanilino)-4-(4-fluoroanilino) pyrimidine (Method 7; 100 mg, 0.25 mmol), N-(3-aminopropyl)-2-pyrrolidinone (38 mg, 0.27 mmol) and 1-hydroxybenzotriazole (44 mg, 0.32 mmol) in DMF (0.5 ml). The mixture was stirred for 16 hours and then a 1:1 mixture of saturated sodium chloride solution and water (10 ml) was added. The precipitated solid was collected by filtration and dried to a constant weight in a vacuum oven at 40° C. to give the product as an off-white solid (98 mg, 75%). MS (MH+): 528; HPLC (RT): 4.01.

EXAMPLES 60–85

The following compounds were prepared by an analogous method to that described in Example 59, using the appropriate 4-anilino-5-bromo-2-(4-carboxyanilino)pyrimidine (Methods 7–13) and the appropriate amine:

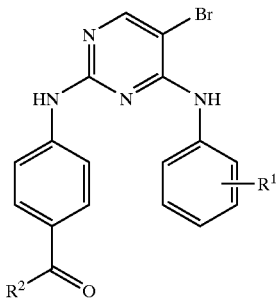

| Ex | R[1] | R[2] (Precursor amine) | MS (MH+) | HPLC (RT) |
|---|---|---|---|---|
| 60 | 4-F | 1-(2-Aminoethyl)pyrrolidine | 499, 501 | 5.11 |
| 61 | 4-F | 1-(2-Aminoethyl)piperidine | 514, 516 | 5.80 |
| 62 | 4-F | 2-Isopropylaminoethylamine[1] | 488, 490 | 4.03 |
| 63 | 3,4-di-F | 1-(3-Aminopropyl)-2-pyrrolidinone | 545, 547 | 4.52 |
| 64 | 3,4-di-F | 1-(2-Aminoethyl)pyrrolidine | 518, 520 | 5.63 |
| 65 | 3,4-di-F | 1-(2-Aminoethyl)piperidine | 531, 533 | 7.09 |
| 66 | 3,4-di-F | 2-Isopropylaminoethylamine[1] | 505, 507 | 4.71 |
| 67 | 4-SMe | 1-(3-Aminopropyl)-2-pyrrolidinone | 555, 557 | 5.18 |
| 68 | 4-SMe | 1-(2-Aminoethyl)pyrrolidine | 527, 529 | 5.08 |
| 69 | 4-SMe | 1-(2-Aminoethyl)piperidine | 541, 543 | 7.12 |
| 70 | 4-SMe | 2-Isopropylaminoethylamine[1] | 516, 518 | 4.84 |
| 71 | 4-Br | 1-(3-Aminopropyl)-2-pyrrolidinone | 589, 591 | 5.72 |
| 72 | 4-Br | 1-(2-Aminoethyl)pyrrolidine | 561, 563 | 6.29 |
| 73 | 4-Br | 1-(2-Aminoethyl)piperidine | 575, 577 | 7.48 |
| 74 | 4-Br | 2-Isopropylaminoethylamine[1] | 549, 551 | 4.56 |
| 75 | 3-Me | 1-(3-Aminopropyl)-2-pyrrolidinone | 523, 525 | 5.10 |
| 76 | 3-Me | 1-(2-Aminoethyl)pyrrolidine | 495, 497 | 5.25 |
| 77 | 3-Me | 1-(2-Aminoethyl)piperidine | 509, 511 | 6.66 |
| 78 | 3-Me | 2-Isopropylaminoethylamine[1] | 483, 485 | 4.72 |
| 79 | 3-F | 1-(3-Aminopropyl)-2-pyrrolidinone | 527, 529 | 4.12 |
| 80 | 3-F | 1-(2-Aminoethyl)pyrrolidine | 499, 501 | 5.69 |
| 81 | 3-F | 1-(2-Aminoethyl)piperidine | 513, 515 | 6.58 |
| 82 | 3-F | 2-Isopropylaminoethylamine[1] | 487, 489 | 6.63 |
| 83 | 2-CH$_2$OH | 1-(3-Aminopropyl)-2-pyrrolidinone | 539, 541 | 2.53 |
| 84 | 2-CH$_2$OH | 1-(2-Aminoethyl)pyrrolidine | 511, 513 | 2.47 |
| 85 | 2-CH$_2$OH | 2-Isopropylaminoethylamine[1] | 499, 501 | 2.15 |

[1]Substituent in 4-position of the 2-anilino of the resulting example is N-(2-isopropylaminoethyl)carbamoyl.

EXAMPLES 86–90

The following compounds were prepared by an analogous method to that described in Example 59, using 2-(4-carboxyanilino)-5-fluoro-4-(4-methoxyanilino)pyrimidine (Method 27) and the appropriate amine:

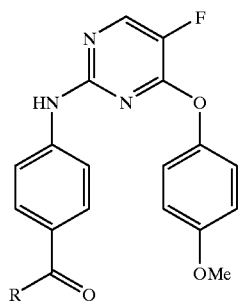

| Ex | R (Precursor amine) | NMR | MS (MH+) |
|---|---|---|---|
| 86 | 4-(2-Amino-ethyl)morpholine | 2.31–2.48(m, 6H), 3.22–3.40(m, 2H), 3.81(s, 3H), 7.05(d, 2H), 7.25(d, 2H), 7.47(d, 2H), 7.55(d, 2H), 8.08–8.17(m, 1H), 8.50(d, 1H), 9.78(s, 1H) | 468 |
| 87 | 1-(2-Amino-ethyl)piperidine | 1.27–1.48(m, 6H), 2.23–2.47(m, 6H), 3.23–3.42(m, 2H), 3.82(s, 3H), 7.05(d, 2H), 7.24(d, 2H), 7.46(d, 2H), 7.54(d, 2H), 8.10(m, 1H), 8.49(d, 1H), 9.78(s, 1H) | 466 |
| 88 | 4-(Dimethyl-amino)benzyl-amine | 2.83(s, 6H), 3.80(s, 3H), 4.30(d, 2H), 6.65(d, 2H), 7.05(d, 2H), 7.11(d, 2H), 7.25(d, 2H), 7.46(d, 2H), 7.60(d, 2H), 8.47(d, 1H), 8.61(t, 1H), 9.78(s, 1H) | 488 |
| 89 | 4-(3-Amino-propyl)morpholine | 1.58–1.71(m, 2H), 2.22–2.40(m, 6H), 3.18–3.32(m, 2H), 3.51–3.60(m, 4H), 3.80(s, 3H), 7.04(d, 2H), 7.23(d, 2H), 7.46(d, 2H), 7.54(d, 2H), 8.14–8.24(m, 1H), 8.47(d, 1H), 9.76(s, 1H) | 482 |
| 90 | 2-(Diiso-propylamino)ethylamine | 0.97(d, 12H), 2.23–2.31(m, 2H), 2.95(sept, 2H), 3.06–3.20(m, 2H), 3.81(s, 3H), 7.04(d, 2H), 7.24(d, 2H), 7.46(d, 2H), 7.56(d, 2H), 8.07(t, 1H), 8.47(d, 1H), 9.77(s, 1H) | 482 |

EXAMPLES 91–98

The following compounds were prepared by an analogous method to that described in Example 59, using the appropriate 5-bromo-2-(4-carboxyanilino)-4-(2-pyridylamino)pyrimidine (Methods 30–31) and the appropriate amine:

| Ex | R¹ | R² (Precursor amine) | MS (MH+) | HPLC (RT) |
|---|---|---|---|---|
| 91 | Me | 1-(3-Aminopropyl)-2-pyrrolidine | 524, 526 | 6.61 |
| 92 | Me | 1-(2-Aminoethyl)pyrrolidine | 496, 498 | 5.10 |
| 93 | Me | 1-(2-Aminoethyl)piperidine | 510, 512 | 7.54 |
| 94 | Me | 2-Isopropylaminoethylamine¹ | 484, 486 | 3.68 |
| 95 | H | 1-(3-Aminopropyl)-2-pyrrolidinone | 510, 512 | 4.00 |
| 96 | H | 1-(2-Aminoethyl)pyrrolidine | 482, 484 | 3.14 |
| 97 | H | 1-(2-Aminoethyl)piperidine | 496, 498 | 4.11 |
| 98 | H | 2-Isopropylaminoethylamine¹ | 470, 472 | 2.80 |

¹Substituent in 4-position of the 2-anilino of the resulting example is N-(2-isopropylaminoethyl)carbamoyl.

EXAMPLES 99–100

The following compounds were prepared by an analogous method to that described in Example 59, using 4-anilino-5-bromo-2-[4-(carboxymethyl)anilino]pyrimidine (Method 32) and the appropriate amine:

| Ex | R (Precursor amine) | MS (MH+) | HPLC (RT) |
|---|---|---|---|
| 99 | 2-(Diisopropylamino)ethylamine | 525.2, 527.2 | 4.81 |
| 100 | 4-(2-Aminoethyl)morpholine | 511.0, 512.9 | 2.52 |

EXAMPLES 101

4-Anilino-5-bromo-2-{4-[3-(dimethylamino)propionamido]anilino}pyrimidine

A solution of dimethylamine in tetrahydrofuran (2.0M; 4 ml) was added to a solution of 4-anilino-5-bromo-2-[4-(3-chloropropionamido)anilino]pyrimidine (Method 37; 60 mg, 0.135 mmol) in DMF (0.2 ml). The solution was heated at 80° C. for 1 hour, diluted with DCM (4 ml) and loaded onto a Varian Mega Bond Elut column. Elution with 0–10%

2.0M methanolic ammonia solution in DCM gave the product (5.4 mg, 9%). MS (MH$^+$): 455, 457; HPLC (RT): 2.70.

EXAMPLE 102

4-Anilino-5-bromo-2-{4-[3-(isopropylamino)propionamido]anilino}pyrimidine

Using an analogous method to that described in Example 101, but starting from 4-anilino-5-bromo-2-[4-(3-chloropropionamido)anilino]pyrimidine (Method 37) and isopropylamine, the product was obtained. MS (MH$^+$): 469, 471; HPLC (RT): 3.70.

EXAMPLE 103

4-Anilino-2-{4-{N-[3-(imidazol-1-yl)propyl]carbamoyl}anilino}-5-methylpyrimidine 4-Anilino-2-chloro-5-methylpyrimidine (Method 23; 219 mg, 1.0 mmol) was dissolved in n-butanol (20 ml) and methanol (4 ml). 4-{N-[3-(imidazol-1-yl)propyl]carbamoyl}aniline (Method 40; 220 mg, 0.9 mmol) and ethereal hydrogen chloride (1.0M; 2 ml, 2.0 mmol) were added and the solution was heated at 100° C. for 20 hours, and then left to stand for 4 days. The solid which separated out was collected by filtration and washed with ether (20 ml) to give the product as a hydrochloride salt (128 mg, 31%). NMR: 2.0–2.1 (m, 2H), 2.2 (s, 3H), 3.2–3.3 (m, 2H), 4.25 (t, 2H), 7.35 (t, 1H), 7.45–7.6 (m, 6H), 7.7 (d, 1H), 7.75 (d, 2H), 7.85 (s, 1H), 8.0 (s, 1H), 8.65 (br t, 1H), 9.25 (s, 1H), 10.0 (br s, 1H), 11.0 (br s, 1H); MS (MH$^+$): 428.2.

EXAMPLE 104

4-Anilino-5-bromo-2-{4-{N-[2-(diethylamino)ethyl]carbamoyl}anilino}pyrimidine

Using an analogous method to that described in Example 103, but starting from 4-{N-[2-(diethylamino)ethyl]carbamoyl}aniline and 4-anilino-5-bromo-2-chloropyrimidine (Method 15), the product was obtained. NMR: 1.0 (t, 6H), 2.4 (m, 4H), 3.3 (m, 4H) 7.2 (t, 1H), 7.4 (t, 2H), 7.6 (t, 6H), 8.1 (bs, 1H), 8.2 (s, 1H), 8.7 (s, 1H), 9.6 (s, 1H); MS (MH$^+$): 483, 485.

EXAMPLES 105–109

The following compounds were prepared by an analogous method to that described in Example 103, using 4-{N-[3-(imidazol-1-yl)propyl]carbamoyl}aniline (Method 40) and the appropriate 5-substituted 4-anilino-2-chloropyrimidine (Methods 16, 22, 24–25):

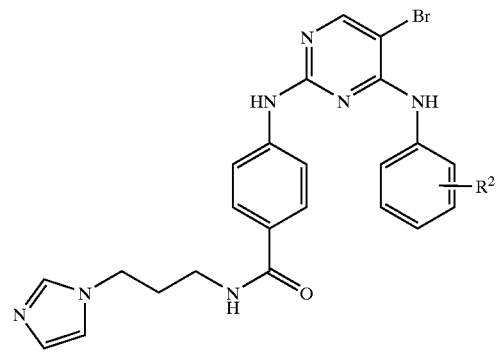

| Ex  | R$^1$ | R$^2$     | NMR | MS (MH$^+$) |
|-----|-------|-----------|-----|-------------|
| 105 | Br    | 2-CH$_2$OH | 1.93(tt, 2H), 3.20(dt, 2H), 4.00(t, 2H), 4.55(s, 2H), 6.88(d, 1H), 7.19(d, 1H), 7.20(dd, 1H), 7.36(d, 1H), 7.40(dd, 1H), 7.63(m, 6H), 7.89(d, 1H), 8.24(t, 1H), 8.26(s, 1H), 9.59(s, 1H) | 522.2, 524.2 |
| 106 | Br    | 4-CH$_2$OH | 1.94(tt, 2H), 3.20(dt, 2H), 4.00(t, 2H), 4.51(d, 2H), 5.18(t, 1H), 6.88(d, 1H), 7.19(d, 1H), 7.32(d, 2H), 7.55(d, 2H), 7.65(m, 5H), 8.21(t, 1H), 8.24(s, 1H), 8.62(s, 1H), 9.53(s, 1H) | 522.5, 524.6 |
| 107 | Br    | 4-F       | 1.94(tt, 2H), 3.20(dt, 2H), 4.00(t, 2H), 6.88(d, 1H), 7.19(d, 1H), 7.21(dd, 2H), 7.60(dd, 2H), 7.63(m, 5H), 8.24(s, 1H), 8.26(t, 1H), 8.73(s, 1H), 9.55(s, 1H) | 510.4, 512.4 |
| 108 | CN    | H         | 1.94(tt, 2H), 3.20(dt, 2H), 4.00(t, 2H), 6.88(d, 1H), 7.19(d, 1H), 7.21(t, 1H), 7.40(dd, 2H), 7.56(d, 2H), 7.65(m, 5H), 8.31(t, 1H), 8.53(s, 1H), 9.59(br. s, 1H), 10.08(s, 1H) | 439 |
| 109 | Cl    | 4-F       | 1.93(tt, 2H), 3.20(dt, 2H), 4.00(t, 2H), 6.87(d, 1H), 7.19(d, 1H), 7.22(dd, 2H), 7.65(m, 7H), 8.17(s, 1H), 8.26(t, 1H), 8.96(s, 1H), 9.57(s, 1H) | 466, 468 |

EXAMPLES 110–113

The following compounds were prepared by an analogous method to that described in Example 103, using 4-{N-[3-(imidazol-1-yl)propyl]carbamoyl}aniline (Method 40) and the appropriate 4-anilino-5-bromo-2-chloropyrimidine (Methods 16–18, 21):

| Ex | R | MS (MH⁺) | HPLC (RT) |
|---|---|---|---|
| 110 | 4-SMe | 538, 540 | 3.30 |
| 111 | 4-Br | 572, 574 | 4.17 |
| 112 | 3,4-di-F | 528, 530 | 3.97 |
| 113 | 3-F | 509.9, 511.7 | 1.79 |

EXAMPLES 114–117

The following compounds were prepared by an analogous method to that described in Example 103, using 4-{N-[3-(imidazol-1-yl)propyl]carbamoyl}aniline (Method 40) and the appropriate 5-substituted 2-chloro-4-(pyridin-2-ylamino)pyrimidine (Methods 33–36):

| Ex | R¹ | R² | NMR | MS (MH⁺) |
|---|---|---|---|---|
| 114 | Br | H | 1.9(m, 2H), 3.2(q, 2H), 4.0(t, 2H), 6.9(s, 1H), 7.2(m, 2H), 7.65(s, 1H), 7.75(s, 4H), 7.8(m, 1H), 8.2(d, 1H), 8.3(t, 1H), 8.4(m, 3H), 9.8(s, 1H) | 493, 495 |
| 115 | Br | Me | 1.9(m, 2H), 2.4(s, 3H), 3.25(q, 2H), 4.0(t, 2H), 6.9(s, 1H), 7.0(d, 1H), 7.2(s, 1H), 7.6(s, 1H), 7.8(m, 5H), 8.05(d, 1H), 8.2(s, 1H), 8.3(t, 1H), 8.4(s, 1H), 9.6(s, 1H) | 507, 509 |
| 116 | Cl | H | 1.9(m, 2H), 3.2(q, 2H), 4.0(t, 2H), 6.9(s, 1H), 7.2(m, 2H), 7.55(s, 1H), 7.65(s, 4H), 7.8(m, 1H), 8.1(d, 1H), 8.3(s, 2H), 8.4(d, 1H), 8.8(s, 1H), 9.8(s, 1H) | 449, 451 |
| 117 | Cl | Me | 1.9(m, 2H), 2.4(s, 3H), 3.2(q, 2H), 4.0(t, 2H), 6.9(s, 1H), 7.1(d, 1H), 7.2(s, 1H), 7.6(s, 1H), 7.8(m, 5H), 8.0(d, 1H), 8.3(m, 2H), 8.5(s, 1H), 9.8(s, 1H) | 463, 465 |

EXAMPLES 118–119

The following compounds were prepared by an analogous method to that described in Example 103, using 4-{N-[3-(imidazol-1-yl)propyl]carbamoyl}aniline (Method 40) and the appropriate 4-substituted 5-bromo-2-chloropyrimidine intermediate (Methods 44–45):

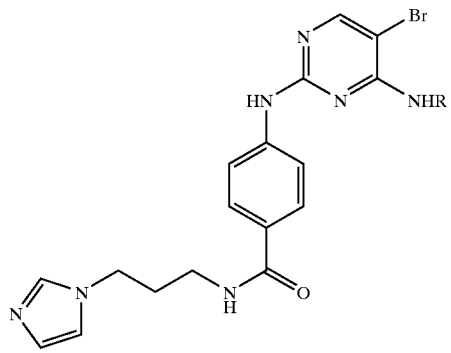

| Ex | R | NMR | MS (MH+) |
|---|---|---|---|
| 118 | 4-methylthiazol-2-yl | 1.9(m, 2H), 2.2(s, 3H), 3.2(q, 2H), 4.0(t, 2H), 6.7(s, 1H), 6.9(s, 1H), 7.2(s, 1H), 7.6(s, 1H), 7.8(m, 4H), 8.3(m, 2H), 9.4(s, 1H) | 513, 515 |
| 119 | 5-methylpyrazol-3-yl | 1.9(m, 2H), 2.2(s, 3H), 3.2(m, 2H), 4.0(t, 2H), 6.4(s, 1H), 6.9(s, 1H), 7.2(s, 1H), 7.6(s, 1H), 7.7(m, 4H), 8.3(m, 2H), 8.4(s, 1H), 12.2(s, 1H) | 496, 498 |

Preparation of Starting Materials

The starting materials for the Examples above are either commercially available or are readily prepared by standard methods from known materials. For example, the following reactions are an illustration, but not a limitation, of some of the starting materials used in the above reactions.

Method 1
4-Anilino-2-(4-carboxyanilino)-5-chloropyrimidine

Ethereal hydrogen chloride (1.0M; 10 ml, 10.0 mmol) was added to a solution of 4-anilino-2,5-dichloropyrimidine (Method 2; 2.41 g, 10.0 mmol) and 4-aminobenzoic acid (1.10 g, 8.0 mmol) in sulpholane (10 ml) and the mixture was heated at 140° C. for 3 hours. The mixture was left to cool and acetone (75 ml) was added. The insoluble solid was collected by filtration and washed with acetone (50 ml) to give the product (2.63 g, 97%). NMR: 7.25 (t, 1H), 7.4 (t, 2H), 7.55–7.65 (m, 4H), 7.7 (d, 2H), 8.35 (s, 1H), 9.6 (br s, 1H), 10.4 (br s, 1H); MS (MH+): 341, 343.

Method 2
4-Anilino-2,5-dichloropyrimidine

A solution of 2,4,5-trichloropyrimidine (Method 3; 5.5 g, 30.0 mmol), aniline (2.79 g, 30.0 mmol) and N,N-diisopropylethylamine (3.87 g, 30.0 mmol) in n-butanol (75 ml) was heated under reflux for 4 hours. Volatile material was removed by evaporation and the residue was dissolved in DCM (100 ml). The solution was washed with water (3×100 ml) and saturated sodium chloride solution (100 ml) and dried. Volatile material was removed by evaporation and the residue was purified by column chromatography on silica gel, eluting with 15% ethyl acetate/isohexane, to give the product as an oil which solidified on standing (3.94 g, 54%). NMR: 7.2 (t, 1H), 7.4 (t, 2H), 7.6 (d, 2H), 8.4 (s, 1H), 9.45 (br s, 1H); MS (MH+): 240, 242, 244.

Method 3
2,4,5-Trichloropyrimidine

5-Chlorouracil (10.0 g, 68.5 mmol) was dissolved in phosphorus oxychloride (60 ml) and phosphorus pentachloride (16.0 g, 77.0 mmol) was added. The mixture was heated under reflux for 16 hours, left to cool and then poured slowly into water (200 ml) with vigorous stirring. The mixture was stirred for 1.5 hours and then ethyl acetate (250 ml) was added. The organic layer was separated and the aqueous layer was extracted with a further portion of ethyl acetate (250 ml). The combined extracts were washed with saturated sodium bicarbonate (200 ml) and saturated sodium chloride solution (200 ml), and then dried. Volatile material was removed by evaporation and the residue was purified by column chromatography, eluting with DCM, to give the product as a yellow liquid (6.37 g, 51%). NMR (CDCl₃): 8.62 (s, 1H); MS (MH+): 182, 184, 186.

Method 4

4-Anilino-5-bromo-2-(3-carboxyanilino)pyrimidine

Using an analogous method to that described in Method 1, but starting from 4-anilino-5-bromo-2-chloropyrimidine and 3-aminobenzoic acid, the product was obtained. NMR: 7.2–7.4 (m, 4H), 7.55–7.6 (m, 3H), 7.8 (dd, 1H), 7.95 (s, 1H), 8.4 (s, 1H), 9.3 (br s, 1H), 10.2 (br s 1H); MS (MH+): 385, 387.

Methods 5–13

The following intermediates were prepared by an analogous method to that described in Method 1, using 4-aminobenzoic acid and the appropriate 5-substituted 4-anilino-2-chloropyrimidine (Methods 14–22):

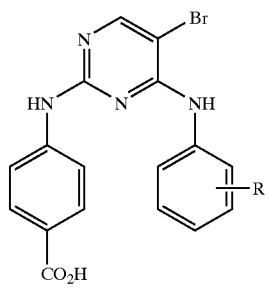

| Method | R | MS (MH+) |
|---|---|---|
| 5 | 4-OMe | 415, 417 |
| 6 | H | 385, 387 |
| 7 | 4-F | 403, 405 |
| 8 | 3,4-di-F | 421, 423 |
| 9 | 4-SMe | 431, 433 |
| 10 | 4-Br | 463, 465, 467 |
| 11 | 3-Me | 399, 401 |
| 12 | 3-F | 403, 405 |
| 13 | 2-CH$_2$OH | 415, 417 |

Methods 14–25

The following intermediates were prepared by an analogous method to that described in Method 2, using the appropriate aniline and the appropriate 5-substituted 2,4-dichloropyrimidine:

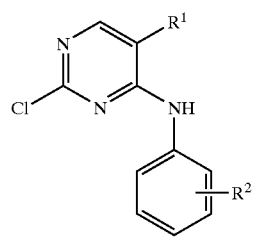

| Method | R$^1$ | R$^2$ | MS (MH+) or NMR |
|---|---|---|---|
| 14 | Br | 4-OMe | 314, 316 |
| 15 | Br | H | 284, 286, 288 |
| 16 | Br | 4-F | 7.22(m, 2H), 7.55(m, 2H), 8.42(s, 1H), 9.32(s, 1H) |
| 17 | Br | 3,4-di-F | 7.42(m, 2H), 7.72(m, 1H), 8.47(s, 1H), 9.37(s, 1H) |
| 18 | Br | 4-SMe | 2.50(s, 3H), 7.27(d, 2H), 7.47(d, 2H) 8.42(s, 1H), 9.23(s, 1H) |
| 19 | Br | 4-Br | 360.0, 362.0, 364.0, 366.0 (MH$^-$) |
| 20 | Br | 3-Me | 298, 300, 302 |
| 21 | Br | 3-F | 6.97(m, 1H), 7.45(m, 3H), 8.48(s, 1H), 9.35(s, 1H) |
| 22 | Br | 2-CH$_2$OH | 314, 316 |
| 23 | Me | H | 220.2, 222.2 |
| 24 | Br | 4-CH$_2$OH | 314, 316, 318 |
| 25 | Cl | 4-F | 258, 260 |

Methods 26–27

The following intermediates were prepared by an analogous method to that described in Method 1, using 4-aminobenzoic acid and the appropriate 5-substituted 4-phenoxy-2-chloropyrimidine (Methods 28–29):

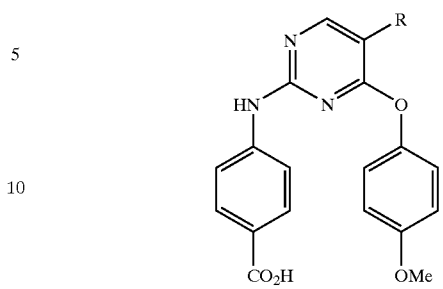

| Method | R | MS (MH+) |
|---|---|---|
| 26 | Br | 416, 418 |
| 27 | F | 356 |

Method 28
5-Bromo-2-chloro-4-(4-methoxyphenoxy)pyrimidine

A mixture of 5-bromo-2,4-dichloropyrimidine (5.0 g, 22.0 mmol), 4-methoxyphenol (2.72 g, 22.0 mmol) and potassium carbonate (6.07 g, 44.0 mmol) in DMF (20 ml) was stirred for 24 hours. The mixture was added to water (100 ml) and the solid which separated out was collected by filtration, washed with water (50 ml) and dried under high vacuum to give the product (6.6 g, 96%). NMR: 3.8 (s, 3H), 7.0 (d, 2H), 7.2 (d, 2H), 8.8 (s, 1H).

Method 29
2-Chloro-5-fluoro-4-(4-methoxyphenoxy)pyrimidine

Using an analogous method to that described in Method 28, but starting from 2,4-dichloro-5-fluoropyrimidine and 4-methoxyphenol, the product was obtained. NMR: 3.84 (s, 3H), 6.79–7.00 (m, 2H), 7.06–7.18 (m, 2H), 8.31–8.36 (m, 1H); MS (M+): 254, 256.

Methods 30–31

The following intermediates were prepared by an analogous method to that described in Method 1, using 4-aminobenzoic acid and the appropriate 5-bromo-2-chloro-4-(2-pyridylamino)pyrimidine (Methods 32–33):

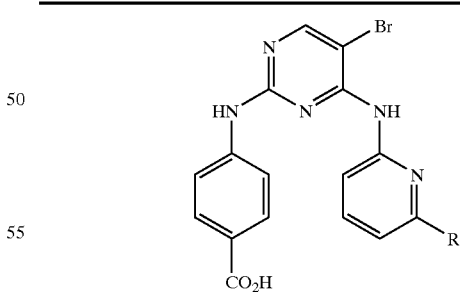

| Method | R | MS (MH+) |
|---|---|---|
| 30 | Me | 400, 402 |
| 31 | H | 386, 388 |

Method 32
4-Anilino-5-bromo-2-[4-(carboxyethyl)anilino]pyrimidine

A mixture of 4-anilino-5-bromo-2-chloropyrimidine (Method 15; 1.50 g, 5.3 mmol), 4-aminophenylacetic acid (0.76 g, 5.0 mmol) and concentrated hydrochloric acid (0.98 ml, 5.3 mmol) in n-butanol (20 ml) was heated at 100° C. for 18 hours. The solid which separated out on cooling was collected by filtration and washed with n-butanol (20 ml) and diethyl ether (20 ml). The solid was dissolved in THF (20 ml) and methanol (10 ml). 2M Sodium hydroxide (3.80 ml, 7.6 mmol) was added and the solution was stirred for 18 hours. Volatile material was removed by evaporation and the residue was partitioned between ether (20 ml) and water (20 ml). The aqueous phase was separated and acidified to pH 3 to give the product as a white solid (350 mg). NMR: 7.0 (d, 2H), 7.2 (m, 1H), 7.4 (m, 2H), 7.5 (d, 2H), 7.6 (d, 2H), 8.2 (s, 1H), 8.6 (s, 1H), 9.3 (s, 1H); MS (MH$^+$); 399, 401.

Methods 33–36

The following intermediates were prepared by an analogous method to that described in Method 2, using the appropriate 2-aminopyridine and the appropriate 5-substituted 2,4-dichloropyrimidine:

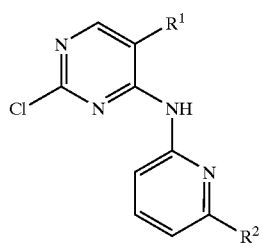

| Method | R$^1$ | R$^2$ | MS (MH$^+$) |
|---|---|---|---|
| 33 | Br | Me | 299, 301 |
| 34 | Br | H | 285, 287 |
| 35 | Cl | H | 240, 242 |
| 36 | Cl | Me | 254, 256 |

Method 37

4-Anilino-5-bromo-2-[4-(3-chloropropionamido)anilino] pyrimidine

Chloropropionyl chloride (0.143 g, 1.13 mmol) was added to a stirred solution of 2-(4-aminoanilino)-4-anilino-5-bromopyrimidine (Method 38; 0.40 g, 1.13 mmol) and triethylamine (0.173 ml, 1.24 mmol) in DMF (1 ml). The mixture was stirred at room temperature and then water (4 ml) was added. The precipitated solid was collected by filtration and washed with ether (1 ml) to give the product (0.21 g, 42%) as a brown solid. MS (MH$^+$): 448, 450.

Method 38

2-(4-Aminoanilino)-4-anilino-5-bromopyrimidine

Sodium hydrosulphite (9.5 g, 54.5 mmol) was added over 30 minutes to a stirred solution of anilino-5-bromo-2-(4-nitroanilino)pyrimidine (Method 39; 7.0 g, 18.2 mmol) in a hot mixture of ethanol and water (1:1, 100 ml). The resulting suspension was stirred for a further two hours and insoluble material was removed by filtration. The filtrate was concentrated and the residue was partitioned between 1M aqueous sodium hydroxide (50 ml), and DCM (100 ml). The organic layer was separated, washed with water (2×10 ml) and dried. Volatile material was removed by evaporation to give the product (4.55 g, 70%). MS (MH$^+$): 356, 358.

Method 39

4-Anilino-5-bromo-2-(4-nitroanilino)pyrimidine

Using an analogous method to that described in Method 1, but starting from 4-anilino-5-bromo-2-chloropyrimidine (Method 15), the product was obtained. MS (MH$^+$): 386, 388.

Method 40

4-{N-[3-(Imidazol-1-yl)propyl]carbamoyl}aniline

A mixture of 4-{N-[3-(imidazol-1-yl)propyl] carbamoyl}nitrobenzene (Method 41; 2.0 g, 7.30 mmol), 10% palladium on carbon (100 mg) cyclohexene (40 ml) and ethanol (80 ml) was heated under reflux under an atmosphere of nitrogen for 4 hours. Two further portions of cyclohexene (40 ml) were added and heating was continued for 1 hour after each addition. The mixture was left to cool and the catalyst was removed by filtration. The filtrate was concentrated by evaporation and the residue was recrystallized from a mixture of ethanol and ether to give the product (1.2 g, 67%). NMR: 1.9–2.0 (m, 2H), 3.1–3.2 (m, 2H), 4.0 (t, 2H), 5.6 (br s 2H), 6.55 (d, 2H), 6.85 (s, 1H), 7.2 (s, 1H), 7.55 (d, 2H), 7.65 (s, 1H), 8.0 (br t, H).

Method 41

4-{N-[3-(Imidazol-1-yl)propyl]carbamoyl}nitrobenzene

A solution of 4-nitrobenzoyl chloride (18.5 g, 0.1 mol) in DCM (200 ml) was added dropwise to a stirred solution of 1-(3-aminopropyl)imidazole (14.0 g, 0.112 mol) and triethylamine (15 ml, 0.107 mol) in DCM (200 ml) at 0° C. The mixture was stirred at 0° C. for 1 hour, and the solid which had separated out was collected by filtration and washed with water (100 ml) and acetone (100 ml) to give the product (21.6 g, 79%). NMR: 1.9–2.0 (m, 2H), 3.2–3.3 (m, 2H), 4.0 (t, 2H), 6.85 (s, 1H), 7.2 (s, 1H), 7.65 (s, 1H), 8.05 (d, 2H), 8.3 (d, 2H), 8.8 (br s, 1H).

Method 42

4-Anilino-5-cyano-2-(methanesulphonyl)pyrimidine

3-Chloroperoxybenzoic acid (57–86%; 2.67 g, 8.8–13.3 mmol) was added in aliquots to a solution of 4-anilino-5-cyano-2-(methylthio)pyrimidine (Method 43; 1.0 g, 4.13 mmol) in chloroform (100 ml), and the mixture was stirred for 2 hours. The mixture was washed with saturated sodium bicarbonate (100 ml), water (100 ml), and saturated sodium chloride (100 ml) and dried. Volatile material was removed by evaporation and the residue was taken up in DCM (10 ml). The solution was loaded onto a silica column pre-equilibrated with 20% ethyl acetate solution in isohexane. Elution with 20–50% ethyl acetate in isohexane and concentration of the appropriate fractions gave the product as a yellow solid (680 mg, 61%). NMR (CDCl$_3$): 3.26 (s, 3H), 7.30 (t, 1H), 7.44 (dd, 2H), 7.57 (d, 2H), 7.65 (br s, 1H), 8.71 (s,1H); MS (MH$^+$): 274.9.

Method 43

4-Anilino-5-cyano-2-(methylthio)pyrimidine

Using a method analogous to that described in Method 2, but starting from 4-chloro-5-cyano-2-(methylthio) pyrimidine (obtained as described in J. Het. Chem. 1971, 8, 445) and performing the reaction at 85° C., the product was obtained. NMR (CDCl$_3$): 2.51 (s, 3H), 7.15 (br s, 1H), 7.20 (t, 1H), 7.40 (dd, 2H), 7.57 (d, 2H), 8.38 (s, 1H).

Methods 44–45

The following intermediates were prepared by an analogous method to that described in Method 2, using the appropriate amino heterocycle and 5-bromo-2,4-dichloropyrimidine:

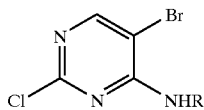

| Method | R | MS (MH⁻) |
|---|---|---|
| 44 | 4-methylthiazol-2-yl | 303, 305 |
| 45 | 5-methylpyrazol-3-yl | 288, 290 |

EXAMPLE 120

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d): Capsule | mg/capsule |
|---|---|
| Compound X | 10 |
| Lactose Ph.Eur | 488.5 |
| Magnesium stearate | 1.5 |

| (e): Injection I | (50 mg/ml) |
|---|---|
| Compound X | 5.0% w/v |
| 1M Sodium hydroxide solution | 15.0% w/v |
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% w/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A pyrimidine compound of the formula (I):

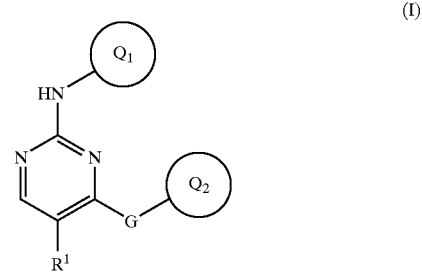

wherein:

$Q_1$ and $Q_2$ are independently selected from aryl or heteroaryl, linked via a ring carbon; and one of $Q_1$ and $Q_2$ or both of $Q_1$ and $Q_2$ is substituted on a ring carbon by one substituent of the formula (Ia) or (Ia'):

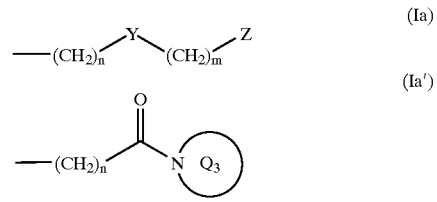

wherein:

Y is —NHC(O)— or —C(O)NH—;

Z is $R^aO$—, $R^bR^cN$—, $R^dS$—, $C_{3-8}$cycloalkyl, phenyl or a heterocyclic group; wherein said phenyl, $C_{3-8}$cycloalkyl or heterocyclic group are optionally substituted on a ring carbon by one or more groups selected from $R^h$; and wherein if said heterocyclic group contains an —NH— moiety that nitrogen may be optionally substituted by a group selected from $R^i$;

$R^a, R^b, R^c, R^d, R^e, R^f$ and $R^g$ are independently selected from hydrogen, $C_{1-4}$alkyl, $C_{2-4}$alkenyl and $C_{3-8}$cycloalkyl; wherein said $C_{1-4}$alkyl, $C_{2-4}$alkenyl and $C_{3-8}$cycloalkyl are optionally substituted by one or more groups selected from $R^j$;

n is 0 or 1;

m is 1, 2 or 3;

$Q_3$ is a nitrogen linked heterocycle; wherein said heterocycle is optionally substituted on a ring carbon by one or more groups selected from $R^k$; and wherein if said heterocyclic group contains an —NH— moiety that nitrogen may be optionally substituted by a group selected from $R^m$;

G is —O— or —$NR^2$—;

$R^2$ is selected from hydrogen, $C_{1-6}$alkyl, $C_{3-6}$alkenyl and $C_{3-6}$alkynyl; wherein said $C_{1-6}$alkyl, $C_{3-6}$alkenyl and $C_{3-6}$alkynyl are optionally substituted by one or more groups selected from $R^n$;

$R^1$ is selected from hydrogen, halo, hydroxy, nitro, amino, N—($C_{1-3}$alkyl)amino, N,N-di-($C_{1-3}$alkyl)amino, cyano, trifluoromethyl, trichloromethyl, $C_{1-3}$alkyl [optionally substituted by 1 or 2 substituents independently selected from halo, cyano, amino, N—($C_{1-3}$alkyl)amino, N,N-di-($C_{1-3}$alkyl)amino, hydroxy and trifluoromethyl], $C_{3-5}$alkenyl [optionally substituted by up to three halo substituents, or by one trifluoromethyl substituent], $C_{3-5}$alkynyl, $C_{1-3}$alkoxy, mercapto, $C_{1-3}$alkylsulphanyl, carboxy and $C_{1-3}$alkoxycarbonyl;

$Q_1$ is optionally substituted on a ring carbon by one to four substituents independently selected from halo, mercapto, nitro, formyl, formamido, carboxy, cyano, amino, ureido, carbamoyl, sulphamoyl, $C_{1-4}$alkyl, $C_{2-4}$alkenyl, $C_{2-4}$alkynyl [wherein said $C_{1-4}$alkyl, $C_{2-4}$alkenyl and $C_{2-4}$alkynyl are optionally substituted by one or more groups selected from $R^o$], $C_{1-4}$alkanoyl, $C_{1-4}$alkoxycarbonyl, heterocyclic group, $C_{1-4}$alkylS(O)$_a$ [wherein a is 0 to 2 and said $C_{1-4}$alkyl is optionally substituted by hydroxy], N'-($C_{1-4}$alkyl)ureido, N',N'-di-($C_{1-4}$alkyl)ureido, N'-($C_{1-4}$alkyl)-N-($C_{1-4}$alkyl)ureido, N',N'-di-($C_{1-4}$alkyl)-N-($C_{1-4}$alkyl)ureido, N—$C_{1-4}$alkylamino, N,N-di-($C_{1-4}$alkyl)amino, N-($C_{1-4}$alkyl)sulphamoyl, N,N-di-($C_{1-4}$alkyl)sulphamoyl, N—$C_{1-4}$alkylcarbamoyl, N,N-di-($C_{1-4}$alkyl)carbamoyl and $C_{1-4}$alkanoylamino;

and also independently, or in addition to, the above substituents, $Q_1$ may be optionally substituted by one to two substituents independently selected from aryl, $C_{3-8}$cycloalkyl and a heterocyclic group; wherein said aryl, $C_{3-8}$cycloalkyl or heterocyclic group may be optionally substituted on a ring carbon by one or more groups selected from $R^p$; and wherein if said heterocyclic group contains an —NH— moiety that nitrogen may be optionally substituted by a group selected from $R^q$;

and also independently, or in addition to, the above substituents, $Q_1$ may be optionally substituted by one $C_{1-4}$alkoxy or by one hydroxy substituent;

$Q_2$ is optionally substituted on a ring carbon by one to four substituents independently selected from halo, hydroxy, mercapto, nitro, formyl, formamido, carboxy, cyano, amino, ureido, carbamoyl, sulphamoyl, $C_{1-4}$alkyl, $C_{2-4}$alkenyl, $C_{2-4}$alkynyl, $C_{1-4}$alkoxy [wherein said $C_{1-4}$alkyl, $C_{2-4}$alkenyl, $C_{2-4}$alkynyl and $C_{1-4}$alkoxy are optionally substituted by one or more groups selected from $R^r$], $C_{1-4}$alkanoyl, $C_{1-4}$alkoxycarbonyl, heterocyclic group, $C_{1-4}$alkylS(O)$_a$ [wherein a is 0 to 2 and said $C_{1-4}$alkyl is optionally substituted by hydroxy], N'($C_{1-4}$alkyl)ureido, N',N'-di-($C_{1-4}$alkyl)ureido, N'-($C_{1-4}$alkyl)-N-($C_{1-4}$alkyl)ureido, N',N'-di-($C_{1-4}$alkyl)-N-($C_{1-4}$alkyl)ureido, N—$C_{1-4}$alkylamino, N,N-di-($C_{1-4}$alkyl)amino, N-($C_{1-4}$alkyl)sulphamoyl, N,N-di-($C_{1-4}$alkyl)sulphamoyl, N—$C_{1-4}$alkylcarbamoyl, N,N-di-($C_{1-4}$alkyl)carbamoyl, $C_{2-4}$alkenyloxy, $C_{2-4}$alkynyloxy, $C_{1-4}$alkanoylamino and a group of formula (Ia) or (Ia') as depicted above;

and also independently, or in addition to, the above substituents, $Q_2$ may be optionally substituted by one to two substituents independently selected from aryl, $C_{3-8}$cycloalkyl or a heterocyclic group; wherein said aryl, $C_{3-8}$cycloalkyl or heterocyclic group may be optionally substituted on a ring carbon by one or more groups selected from $R^s$; and wherein if said heterocyclic group contains an —NH— moiety that nitrogen may be optionally substituted by a group selected from $R^t$;

$R^j$, $R^n$, $R^o$ and $R^r$ are independently selected from hydroxy, halo, amino, cyano, formyl, formamido, carboxy, nitro, mercapto, carbamoyl, sulphamoyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy, $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N-($C_{1-4}$alkyl)sulphamoyl, N-($C_{1-4}$alkyl)$_2$sulphamoyl, N-($C_{1-4}$alkyl)carbamoyl, N-($C_{1-4}$alkyl)$_2$carbamoyl, phenyl, phenylthio, phenoxy, $C_{3-8}$cycloalkyl and a heterocyclic group; wherein said phenyl, phenylthio, phenoxy, $C_{3-8}$cycloalkyl or heterocyclic group may be optionally substituted on a ring carbon by one or more groups selected from $R^u$; and wherein if said heterocyclic group contains an —NH— moiety that nitrogen may be optionally substituted by a group selected from $R^v$;

$R^h$, $R^k$, $R^p$, $R^s$ and $R^u$ are independently selected from hydroxy, halo, amino, cyano, formyl, formamido, carboxy, nitro, mercapto, carbamoyl, sulphamoyl, $C_{1-4}$alkyl [optionally substituted by one or more groups selected from halo, cyano, amino, N—$C_{1-4}$alkylamino, N,N-di-($C_{1-4}$alkyl)amino or hydroxy], $C_{2-4}$alkenyl [optionally substituted by one or more groups selected from halo], $C_{2-4}$alkynyl, N—$C_{1-4}$alkylamino, N,N-di-($C_{1-4}$alkyl)amino, $C_{1-4}$alkanoyl, $C_{1-4}$alkanoyloxy, $C_{1-4}$alkoxy [optionally substituted by one or more groups selected from halo], $C_{1-4}$alkoxycarbonyl, N—$C_{1-4}$alkylcarbamoyl, N,N-di-($C_{1-4}$alkyl)carbamoyl, $C_{1-4}$alkanoylamino, $C_{1-4}$alkylS(O)$_a$ wherein a is 0 to 2, $C_{1-4}$alkylsulphonylamino, N-($C_{1-4}$alkyl)sulphamoyl, N-($C_{1-4}$alkyl)$_2$sulphamoyl, phenyl, $C_{3-8}$cycloalkyl and a heterocyclic group; and $R^i$, $R^q$, $R^t$ and $R^v$ are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl;

or a pharmaceutically acceptable salt or in vivo hydrolysable ester formed from an available carboxy or hydroxy group thereof.

2. A pyrimidine compound according to claim 1 wherein $Q_1$ is phenyl or a pharmaceutically acceptable salt or in vivo hydrolysable ester formed from an available carboxy or hydroxy group thereof.

3. A pyrimidine compound according to claim 1 wherein $Q_2$ is phenyl, pyridyl, thiazolyl or pyrazolyl or a pharmaceutically acceptable salt or in vivo hydrolysable ester formed from an available carboxy or hydroxy group thereof.

4. A pyrimidine compound according to claim 1 wherein the substituent (Ia) or (Ia') is N-[2-(3-aza-8-oxabicyclo[3,2,1]hex-3-yl)ethyl]carbamoyl, N-(2-di-n-butylaminoethyl)carbamoyl, N-(2-diethylaminoethyl)carbamoyl, N-(2-diisopropylaminoethyl)carbamoyl, N-[2-(3,5-dimethylpyrazol-1-yl)ethyl]carbamoyl, N-(2-indol-3-ylethyl)carbamoyl, N-(2-isopropylaminoethyl)carbamoyl, N-[2-(2-methyl-5-nitroimidazol-1-yl)ethyl]carbamoyl, N-(2-methylthioethyl)carbamoyl, N-(2-morpholinoethyl)carbamoyl, N-(2-piperidin-1-ylethyl)carbamoyl, N-(2-pyrrolidin-1-ylethyl)carbamoyl, N-(2-thien-2-ylethyl)carbamoyl, N-(2-thiomorpholinoethyl)carbamoyl, N-(3-n-butoxypropyl)carbamoyl, N-(3-di-n-butylaminopropyl)carbamoyl, N-(3-imidazol-1-ylpropyl)carbamoyl, N-[3-(4-methylpiperazin-1-yl)propyl]carbamoyl, N-(3-methylthiopropyl)carbamoyl, N-(3-morpholinopropyl)

carbamoyl, N-[3-(2-oxpyrrolidin-1-yl)propyl]
carbamoyl, N-(3-pyrrolidin-1-yl)carbamoyl,
N-(2-di-isopropylaminoethyl)carbamoylmethyl, N-(2-morpholinoethyl)carbamoylmethyl, N-(4-dimethylaminobenzylamine)carbamoyl, N-(imidazo[1,2-a]pyrid-2-ylmethyl)carbamoyl, N-(5-methylfur-2-ylmethyl)carbamoyl, 4-(pyrrolidin-1-yl)piperidin-1-ylcarbonyl, 3-(dimethylamino)propanamide or 3-(isopropylamino)propanamide or a pharmaceutically acceptable salt or in vivo hydrolysable ester formed from an available carboxy or hydroxy group thereof.

5. A pyrimidine compound according to claim 1 wherein the substituent of formula (Ia) or (Ia') is on ring $Q_1$ or a pharmaceutically acceptable salt or in vivo hydrolysable ester formed from an available carboxy or hydroxy group thereof.

6. A pyrimidine compound according to claim 1 wherein when $Q_1$ is phenyl the substituent of formula (Ia) or (Ia') is in either the para- or meta-position relative to the —NH— or a pharmaceutically acceptable salt or in vivo hydrolysable ester formed from an available carboxy or hydroxy group thereof.

7. A pyrimidine compound according to claim 1 wherein G is —O— or —NH— or a pharmaceutically acceptable salt or in vivo hydrolysable ester formed from an available carboxy or hydroxy group thereof.

8. A pyrimidine derivative according to claim 1 wherein $R^1$ is fluoro, chloro, bromo, methyl or cyano or a pharmaceutically acceptable salt or in vivo hydrolysable ester formed from an available carboxy or hydroxy group thereof.

9. A pyrimidine compound according to claim 1 wherein $Q_1$ is unsubstituted except by the substituent of formula (Ia) or (Ia') or a pharmaceutically acceptable salt or in vivo hydrolysable ester formed from an available carboxy or hydroxy group thereof.

10. A pyrimidine compound according to claim 1 wherein $Q_2$ is unsubstituted or substituted by one or two groups selected from fluoro, bromo, methyl, methoxy, methylthio or hydroxymethyl or a pharmaceutically acceptable salt or in vivo hydrolysable ester formed from an available carboxy or hydroxy group thereof.

11. A pyrimidine compound according to claim 1 selected from:
2-{4-[N-(3-imidazol-1-ylpropyl)carbamoyl]anilino}-4-anilino-5-bromopyrimidine;
2-{4-[N-(2-pyrrolidin-1-ylethyl)carbamoyl]anilino}-4-(3-fluoroanilino)-5-bromopyrimidine;
2-{4-[N-(2-isopropylaminoethyl)carbamoyl]anilino}-4-(3-fluoroanilino)-5-bromopyrimidine;
2-{4-[N-(2-pyrrolidin-1-ylethyl)carbamoyl]anilino}-4-(2-hydroxymethylanilino)-5-bromopyrimidine;
2-{4-[N-(2-isopropylaminoethyl)carbamoyl]anilino}-4-(2-hydroxymethylanilino)-5-bromopyrimidine;
2-{4-[N-(2-pyrrolidin-1-ylethyl)carbamoyl]anilino}-4-(6-methylpyrid-2-ylamino)-5-bromopyrimidine;
2-{4-[N-(2-isopropylaminoethyl)carbamoyl]anilino}-4-(6-methylpyrid-2-ylamino)-5-bromopyrimidine;
2-{4-[N-(2-pyrrolidin-1-ylethyl)carbamoyl]anilino}-4-(pyrid-2-ylamino)-5-bromopyrimidine;
2-{4-[N-(3-imidazol-1-ylpropyl)carbamoyl]anilino}-4-(pyrid-2-ylamino)-5-bromopyrimidine;
2-{4-[N-(3-imidazol-1-ylpropyl)carbamoyl]anilino}-4-(6-methylpyrid-2-ylamino)-5-bromopyrimidine;
or pharmaceutically acceptable salt or in vivo hydrolysable ester formed from an available carboxy or hydroxy group thereof.

12. A process for preparing a compound of formula (I) or pharmaceutically acceptable salt or in vivo hydrolysable ester thereof as claimed in claim 1 which is:

a) for compounds of formula (I) where G is —NR²—; reacting a pyrimidine of formula (II):

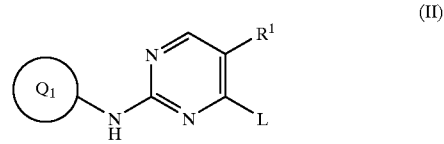

(II)

wherein L is a displaceable group as defined below, with a compound of formula (III):

(III)

where G is —NR²—;

b) reaction of a pyrimidine of formula (IV):

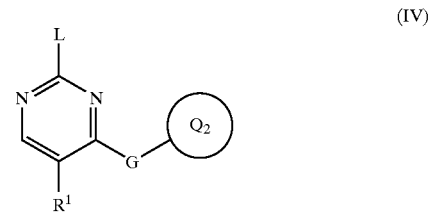

(IV)

wherein L is a displaceable group as defined below, with a compound of formula (V):

(V)

c) for compounds of formula (I) wherein the sidechain is of formula (Ia) and Y is —C(O)NH—; by reaction of an acid of formula (VI):

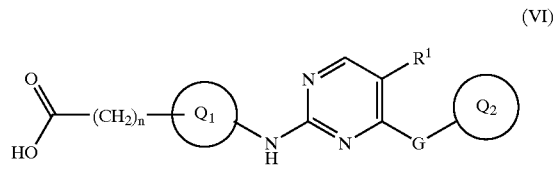

(VI)

or an activated derivative thereof, with an amine of formula (VII):

Z—(CH₂)ₘ—NH₂ (VII)

d) for compounds of formula (I) wherein the sidechain is of formula (Ia) and Y is —NHC(O)— by reaction of an amine of formula (VIII):

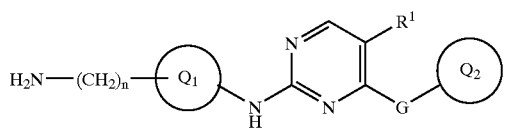

(VIII)

with an acid of formula (IX):

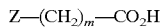

(IX)

or an activated derivative thereof;
e) for compounds of formula (I) wherein the sidechain is of formula (Ia'); by reaction of an acid of formula (VI) (or an activated derivative thereof) with an amine of formula (X):

(X)

and thereafter if necessary:
i) converting a compound of the formula (I) into another compound of the formula (I);
ii) removing any protecting groups;
iii) forming a pharmaceutically acceptable salt or in vivo hydrolysable ester formed from an available carboxy or hydroxy group thereof.

13. A pharmaceutical composition which comprises a pyrimidine compound of the formula (I), or a pharmaceutically acceptable salt or in vivo hydrolysable ester formed from an available carboxy or hydroxy group thereof, as claimed in any one of claims 1 to 11, in association with a pharmaceutically acceptable diluent or carrier.

14. A method for producing a FAK enzyme inhibitory effect in a warm-blooded animal in need of such treatment, which comprises administering to said animal an effective amount of a compound of formula (I) or a pharmaceutically acceptable salt or in vivo hydrolysable ester formed from an available carboxy or hydroxy group thereof as claimed in claim 1.

15. A method for producing a selective CDK2, CDK4 or CDK6 enzyme inhibitory effect in a warm-blooded animal in need of such treatment, which comprises administering to said animal an effective amount of a compound of formula (I) or a pharmaceutically acceptable salt or in vivo hydrolysable ester formed from an available carboxy or hydroxy group thereof as claimed in claim 1.

* * * * *